United States Patent
Walker et al.

(10) Patent No.: US 6,302,844 B1
(45) Date of Patent: Oct. 16, 2001

(54) PATIENT CARE DELIVERY SYSTEM

(75) Inventors: Jay S. Walker, Ridgefield; Magdalena Mik, Greenwich, both of CT (US); Jason Krantz, Madison, WI (US); James A. Jorasch, Stamford, CT (US)

(73) Assignee: Walker Digital, LLC, Stamford, CT (US)

( * ) Notice: Subject to any disclaimer, the term of this patent is extended or adjusted under 35 U.S.C. 154(b) by 0 days.

(21) Appl. No.: 09/282,132

(22) Filed: Mar. 31, 1999

(51) Int. Cl.[7] ............................................. A61B 5/00
(52) U.S. Cl. ........................... 600/300; 128/904; 705/3
(58) Field of Search ................................. 600/300–301; 128/903, 904; 705/2, 3

(56) References Cited

U.S. PATENT DOCUMENTS

| | | | |
|---|---|---|---|
| 5,724,025 | * | 3/1998 | Tavori ................................. 600/300 |
| 5,782,878 | * | 7/1998 | Morgan et al. ...................... 128/904 |
| 5,785,650 | * | 7/1998 | Akasaka et al. .................... 600/300 |
| 5,950,632 | * | 9/1999 | Reber et al. ........................ 128/904 |

OTHER PUBLICATIONS

Mary E. Thyfault, "Users Tun To Audio Systems, (some prefer audioconferencing over videoconferencing because it uses less bandwidth)", Informationweek, Copyright 1997.

"Swedish Startup Sells Telemedics To The US", Computergram International, Newswire, Data Services Ltd., Copyright 1998.

* cited by examiner

Primary Examiner—Eric F. Winakur
Assistant Examiner—Michael Astorino
(74) Attorney, Agent, or Firm—Dean P. Alderucci

(57) ABSTRACT

A method and apparatus for analyzing data from remote monitoring equipment, such as patient telemetry devices, and determining (i) whether an anomalous event has occurred, (ii) if an anomalous event has occurred, whether a physician should be contacted, and (iii) if a physician should be contacted, selecting the physician to contact. Further, the system operates in parallel, in that a plurality of experts (e.g., physicians) may be contacted in response to a single or multiple anomalous events, thus ensuring an efficient response to an anomalous event.

36 Claims, 15 Drawing Sheets

| ALERT 310 | SYSTEM REACTION 320 |
|---|---|
| VENTRICULAR FIBRILLATION | SUMMON AMBULANCE; OFFER CASE TO CARDIOLOGIST(S) |
| LOSS OF CONSCIOUSNESS | SUMMON AMBULANCE; OFFER CASE TO ER PHYSICIAN(S) |
| ABERRANT BLOOD GLUCOSE LEVELS | INSTRUCT PATIENT TO TAKE INSULIN; IF LEVELS DO NOT RETURN TO NORMAL AFTER 15 MINUTES, OFFER CASE TO NURSE(S) |
| FETAL HEART MONITOR ALARM | ALERT MOTHER; INSTRUCT HER TO GO TO HOSPITAL; OFFER CASE TO OBSTETRICIAN(S) |
| TACHYCARDIA | OFFER CASE TO CARDIOLOGIST(S); QUERY PATIENT AS TO ACTIVITY LEVEL |
| ACUTELY HIGH BLOOD PRESSURE | OFFER CASE TO INTERNIST(S); QUERY PATIENT AS TO ACTIVITY LEVEL |

Rows labeled R31–R36 from top to bottom. Table reference: 305.

FIG. 3

| PHYSICIAN'S NAME 410 | PHYSICIAN IDENTIFIER 420 | PHYSICIAN CRITERIA CODES 430 | SPECIALTY 440 | PREVIOUS CASE IDENTIFIERS 450 | AVAILABILITY 460 | CONTACT INFORMATION 470 |
|---|---|---|---|---|---|---|
| JOHN DOE | 123456 | UH, BS, M33, MP | EMERGENCY MEDICINE | C987654, C876543, C765432 | YES | P555-1234 |
| BOB SMITH | 234567 | UH, M33, MP | CARDIOLOGY | C654321, C543210 C432109 | NO | V555-2345 |
| REBECCA ANDERSON | 345678 | BS, BC, U33, FP | NEURO-PATHOLOGY | C321098 | YES | DR@HOSPITAL.COM |
| JANE DOE | 456789 | UH, BS, BC, M33, FP | OB/GYN | C210987, C109876, C098765 | NO | DR@AD.COM |
| JENNIFER ROGERS | 567890 | UH, BS, BC, L33, FP | CARDIOLOGY | C998765,C887654, C776543,C665432 | YES | P555-3456 |
| EILEEN SHIN | 678901 | M33, FP | PATHOLOGY | C554321, C443210 | NO | P555-4567 |
| ANDREW FROTH | 789012 | UH, BS, BC, L33, MP | INTERNAL MEDICINE | C332109,C221098, C110987,C009876 | YES | P555-6789 |
| ALEX SCHWARTZ | 890123 | UH, BS, BC, MP | ENDO-CRINOLOGY | C999876, C888765 | ONLY ABOVE $150.00 | GOOD_DOC@HOSPITAL.COM |
| FAUSTO COPPI | 9012345 | L33, MP | PODIATRY | NULL | YES | V555-8901 |

| PHYSICIAN CRITERION 510 | PHYSICIAN CRITERION CODE 520 |
|---|---|
| UNIVERSAL HEALTH APPROVED PHYSICIAN | UH |
| BLUE SHIELD APPROVED PHYSICIAN | BS |
| BOARD CERTIFIED PHYSICIAN | BC |
| FEE STRUCTURE IN UPPER 33RD PERCENTILE | U33 |
| FEE STRUCTURE IN MIDDLE 33RD PERCENTILE | M33 |
| FEE STRUCTURE IN LOWER 33RD PERCENTILE | L33 |
| MALE | MP |
| FEMALE | FP |

RA51 → (Universal Health Approved Physician)
RA52 → (Blue Shield Approved Physician)
RA53 → (Board Certified Physician)
RA54 → (Fee Structure in Upper 33rd Percentile)
RA55 → (Fee Structure in Middle 33rd Percentile)
RA56 → (Fee Structure in Lower 33rd Percentile)
RA57 → (Male)
RA58 → (Female)

FIG. 5A

| | PATIENT CRITERION 530 | PATIENT CRITERION CODE 540 | PATIENT CRITERION 530 | PATIENT CRITERION CODE 540 | |
|---|---|---|---|---|---|
| RB51 → | REQUIRE UNIVERSAL HEALTH APPROVED PHYSICIAN | R-UH | REQUIRE BOARD CERTIFICATION | R-BC | ← RB58 |
| RB52 → | PREFER UNIVERSAL HEALTH APPROVED PHYSICIAN | P-UH | PREFER BOARD CERTIFICATION | P-BC | ← RB59 |
| RB53 → | REQUIRE BLUE SHIELD APPROVED PHYSICIAN | R-BS | REQUIRE MALE PHYSICIAN | R-MP | ← RB510 |
| RB54 → | PREFER BLUE SHIELD APPROVED PHYSICIAN | P-BS | PREFER MALE PHYSICIAN | P-MP | ← RB511 |
| RB55 → | PREFER FEE STRUCTURE IN UPPER 33RD PERCENTILE | P-U33 | REQUIRE FEMALE PHYSICIAN | R-FP | ← RB512 |
| RB56 → | PREFER FEE STRUCTURE IN MIDDLE 33RD PERCENTILE | P-M33 | PREFER FEMALE PHYSICIAN | P-FP | ← RB513 |
| RB57 → | PREFER FEE STRUCTURE IN LOWER 33RD PERCENTILE | P-L33 | REQUIRE FIRST AVAILABLE PHYSICIAN | R-FA | ← RB514 |

FIG. 5B

| PATIENT'S NAME 610 | PATIENT IDENTIFIER 620 | PATIENT CRITERIA CODES 630 | CURRENTLY BEING TREATED FOR 640 | PAST ALERTS 650 |
|---|---|---|---|---|
| OLIVIA AIOLI | 123456 | P-UH, R-BC, P-U33, P-FP R-FA | GENERAL HEALTH | NONE |
| CHIEN DEGUERRE | 234567 | UH, M33, MP | HIGH HEART ATTACK RISK FACTOR | VENTRICULAR FIBRILLATION 2/13/98 |
| ELIZABETH SMITH | 345678 | R-BC, R-FA | HIGH BLOOD PRESSURE | NONE |
| SVEN TOLFGAARD | 456789 | P-UH, P-M33 | HIGH BLOOD PRESSURE | ACUTELY HIGH BLOOD PRESSURE 3/15/98 |
| DON PURNELL | 567890 | P-BS, P-M33, P-BC | HIGH HEART ATTACK RISK FACTOR | NONE |
| MATT SMITH | 678901 | P-MP, P-U33, P-BC | GENERAL HEALTH | LOSS OF CONSCIOUSNESS 1/1/98 |
| TEUN VAN VLIET | 789012 | R-UH, P-L33 | ARTERIOSCLEROSIS | NONE |
| ANA NG | 890123 | R-BS, P-BC, R-FP | POSSIBLE PREGNANCY COMPLICATIONS | NONE |

FIG. 6

| DATE 710 | CASE IDENTIFIER 720 | PATIENT IDENTIFIER 730 | PHYSICIAN IDENTIFIER 740 | EVENT DESCRIPTION 750 | OUTCOME 760 | OFFERS MADE (PHYSICIAN ID, DOLLAR VALUE OFFERED) 770 | OFFERS ACCEPTED (PHYSICIAN ID, DOLLAR VALUE ACCEPTED) 780 |
|---|---|---|---|---|---|---|---|
| 1/1/98 | 678901A | 678901 | 123456 | LOSS OF CONSCIOUSNESS | ADMITTED TO HOSPITAL FOR NARCOTICS O/D | 123456 - $180.00; 789012 - $200.00; 406961 - $220.00 | 123456 - $180.00; 789012 - $200.00 |
| 1/11/98 | 505995A | 505995 | 567890 | ACUTE HIGH BLOOD PRESSURE | PATIENT QUERIED, FOUND TO BE EXERCISING | 234567 - $375.00; 567890 - $375.00; 961642 - $385.00 | 567890 - $375.00; 234567 - $375.00 |
| 2/14/98 | 381884A | 381884 | 567890, 234567 | TACHYCARDIA | ADMITTED TO HOSPITAL | 567890 - $350.00; 234567 - $375.00 | 567890 - $350.00; 234567 - $375.00 |
| 3/15/98 | 567890A | 567890 | 234567 | ACUTE HIGH BLOOD PRESSURE | E/R ADMINISTERED APPROPRIATE DRUGS AND RELEASED PATIENT | 234567 - $350.00; 567890 - $375.00; 234567 - $375.00; 234567 - $400.00 | 234567 - $400.00 |

PATIENT CARE DELIVERY SYSTEM

BACKGROUND OF THE DISCLOSURE

1. Field of the Invention

This invention generally relates to patient care diagnosis delivery and, more particularly, to facilitating, in exchange for compensation, the provision of an expert diagnosis opinion of a condition based upon data gathered from a remote monitor.

2. Description of the Prior Art

It is known to remotely monitor human physiological parameters such as heart rate, blood pressure, brain waves and the like in patients. Such monitoring may be accomplished using remote monitoring, thereby allowing patients to have freedom of movement. For example, some systems use cellular telephone technology to allow patients to live at home. The patient visits the hospital if the telemetry device indicates that a visit is warranted.

Hewlett-Packard's ECGStat software for its PalmVue handheld computer system allows emergency room clinicians to capture and transmit full 12-lead ECG data, including waveforms, computerized analysis and patient notes to cardiac specialists outside the hospital. It is a wireless system that uses paging technology to transmit data to a physician's handheld computer.

It is well known to use ECG monitors in conjunction with software to analyze patterns in patients' heartbeats. Typically, monitoring technicians (or monitors) are alerted to the possibility that something is amiss by an alarm. Upon examining a readout of the vital sign in question, the monitor makes a decision about (i) whether the patient requires attention (ii) whether the patient requires a cardiologist's services and if so, (iii) which cardiologist to call. Typically, the technician selects the cardiologist from a list of available specialists. This list is substantially determined by availability, i.e., who is on call at the time. If a cardiologist is required, the technician must communicate to a cardiologist the patient's condition over voice or data lines. The technician may use the Hewlett-Packard ECGStat system described above to communicate with the cardiologist.

Monitoring technicians must watch and wait for alarms to go off in all of the above-described systems. They may miss certain subtle warning signs, and if several alarms go off at once, they can only respond to one at a time. Additionally, they must find out which doctors are on call at the time and then contact the appropriate physician. If the "first choice" physician is not available, the technician must then try to contact another physician. In other words, the technician must operate in a serial manner to procure an expert opinion.

Therefore, it is seen to be desirable to provide a system able to analyze a signal from remote monitoring equipment, e.g., medical monitoring equipment, in such a way as to make a preliminary decision about whether or not an expert, such as a physician, should be contacted and to decide which physician or physicians to contact. Moreover, it is seen to be desirable to provide a system that allows physicians and other experts to accept or decline offers made by the system to render a diagnosis, thereby implementing a "piecework" type of compensation structure within the confines of, e.g., the medical environment. Preferably, such a system minimizes or eliminates the human fallibility involved in noticing alarms and contacting experts in a timely manner.

SUMMARY OF THE INVENTION

The invention is a method and apparatus for analyzing data from remote monitoring equipment, such as a patient telemetry device, and determining (i) if an anomaly exists, (ii) if an anomaly does exist, what kind of action should be taken, and (iii) if a physician should be contacted, which one. Further, the system operates in parallel, in that a plurality of experts (e.g., physicians) may be contacted in response to multiple anomalous events, thus ensuring the quickest possible response time.

A method for procuring a diagnosis according to the invention comprises the steps of: receiving representative data that represents at least one physiological parameter of a patient; determining whether the received data is indicative of a physiological anomaly; selecting at least one expert to provide an expert opinion regarding the indicated anomaly; communicating, to the at least one selected expert, the physiological representative data, including the determined anomaly; and receiving, from at least one selected expert, a diagnosis of the anomaly.

A diagnostic procurement system according to the invention comprises: a monitor, for monitoring at least one parameter associated with an entity and communicating data representing the at least one entity parameter; and a controller, responsive to the data representing the at least one entity parameter, for determining whether anomalous entity operational parameters are present and, in the case of anomalous entity operational parameters being present, procuring a diagnosis from at least one of a predetermined number of experts.

BRIEF DESCRIPTION OF THE DRAWINGS

The teachings of the present invention can be readily understood by considering the following detailed description in conjunction with the accompanying drawings, in which:

FIG. 3 depicts an exemplary reaction database in tabular form suitable for use in the central server of FIGS. 1 and 2;

FIG. 4 depicts an exemplary physician database in tabular form suitable for use in the central server of FIGS. 1 and 2;

FIG. 5A depicts an exemplary physician criteria database in tabular form suitable for use in the central server of FIGS. 1 and 2;

FIG. 5B depicts an exemplary patient criteria database in tabular form suitable for use in the central server 200 of FIGS. 1 and 2;

FIG. 6 depicts an exemplary patient database in tabular form suitable for use in the central server 200 of FIGS. 1 and 2;

FIG. 7 depicts an exemplary event database 700 in tabular form suitable for use in the central server of FIGS. 1 and 2;

To facilitate understanding, identical reference numerals have been used, where possible, to designate identical elements that are common to the figures.

DETAILED DESCRIPTION

Figure 1:
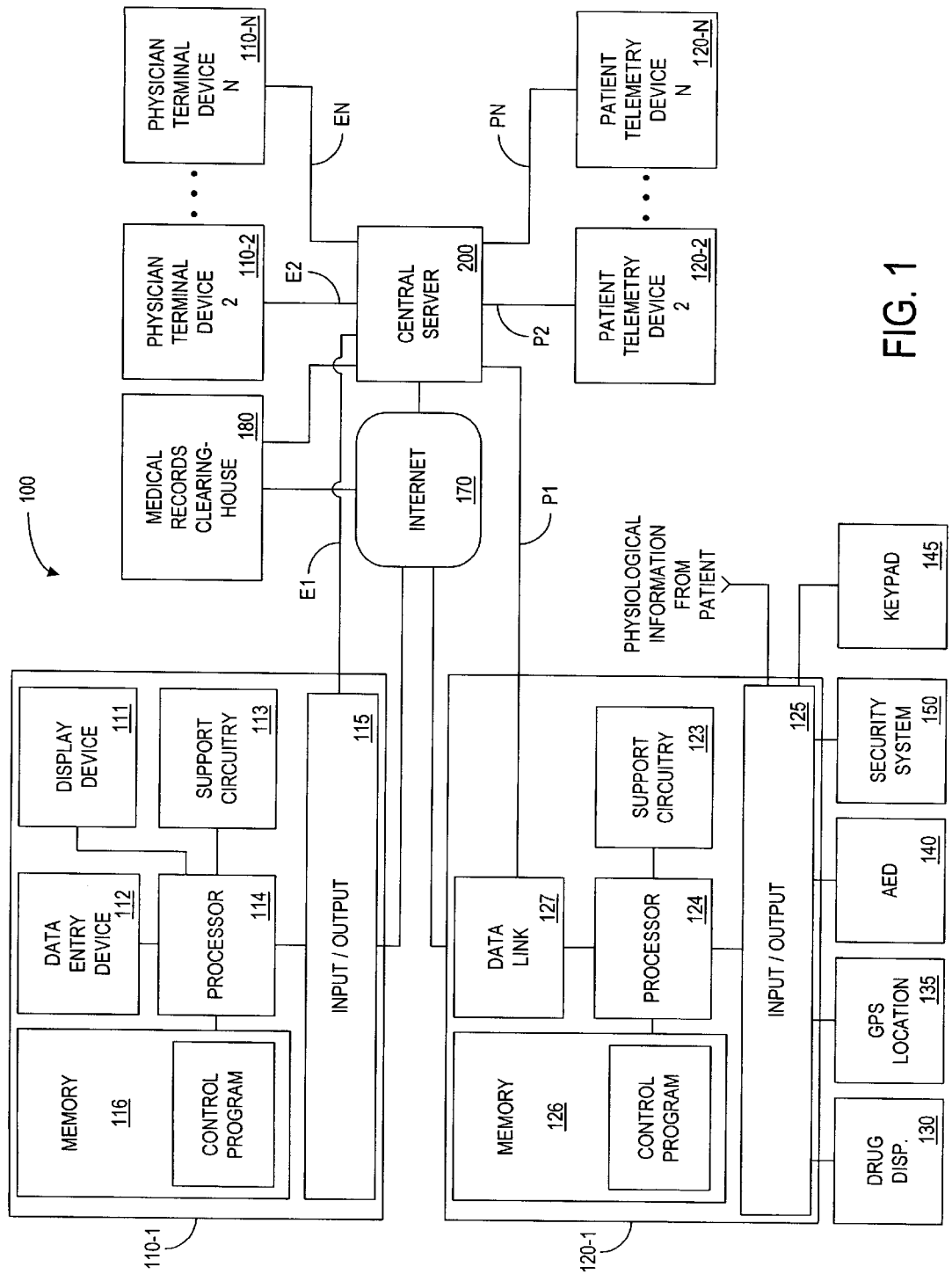
FIG. 1 depicts a high level block diagram of a patient care diagnosis delivery system.

After considering the following description, those skilled in the art will clearly realize that the teachings of the present invention can be readily utilized in any environment in which an entity (e.g., a patient) having at least one monitored operating parameter (e.g., physiological parameter) may require an expert diagnostic or other opinion if one or more of the monitored operating parameters indicates that an operating anomaly is present. The system and method provides (a) an initial screening and decision capability based upon the received operating data sufficient to determine which type of expert is needed; (b) an identification and communication of at least a portion of the operating data to one or more appropriate experts; (c) a transactional capability defining a level of compensation to be provided to the expert in exchange for the rendering of an expert diagnosis regarding the anomaly; and (d) an adaptation of an existing communications infrastructure to the procurement of the expert opinion(s).

While the invention will be primarily described within the context of a medical monitoring system, it will be appreciated by those skilled in the art that the invention has applicability well beyond the patient care diagnosis delivery system described herein. Specifically, the invention comprises, in general terms, a centralized system procuring expert diagnosis or diagnostic opinion(s) in response to remotely monitored data indicative of an event requiring such an opinion.

Throughout this description various terms are used to describe the invention. Unless modified by the following description, several of the terms are defined as follows: An anomaly comprises a dysfunction or precursor to a dysfunction within a monitored entity, such as a patient in a medical monitoring environment. An "expert" is an entity that provides a diagnosis relating to an anomaly. An expert is one deemed by the patient and, optionally, the system, as having expertise in treating the patient's condition. In the case of standard medical specialties, the patient and system will be in agreement as to the definition of an expert. If the patient believes in practitioners of non-standard or alternative therapies, then the system and patient may disagree. A "diagnosis" or diagnostic opinion comprises an identification of an anomaly, a recommended treatment for a patient or any expert opinion tending to remediate or ameliorate an anomalous condition. "Communication" comprises any means of transferring data to or from a communicating party, such as a patient telemetry device, a central server, a physician terminal device, a computing device or telephonic device and the like. A communication may utilize encryption/decryption protocols. "Alert information" comprises information, including local diagnostic information, real time physiological data and other information intended to be used in the rendering of a diagnosis or a determination of the type of expert needed to render such a diagnosis. A data profile is a data template against which raw or processed information is compared to produce a level of affinity between the information and the data profile. A high level of affinity indicates that the information may conform to an anomalous condition associated with the data profile. Profiles may be individualized and adapted to patients. For example, a baseline profile may be adapted over time in response to a patient's improving or degrading condition (e.g., diminished heart valve integrity will lead to changes in ECG data as the heart adapts by pumping harder and/or differently).

FIGS. 1 depicts a high level block diagram of a patient care diagnosis delivery system. Specifically, FIGS. 1 depicts a high level block diagram of a patient care diagnosis delivery system 100 comprising a plurality of physician terminal devices 110-1 through 110-N, a central server 200 and a plurality of patient telemetry devices 120-1 through 120-N.

Each of the plurality of patient telemetry devices 120-1 through 120-N is capable of monitoring at least one physiological parameter of a patient and communicating data representative of the monitored parameter to the central server 200 via respective data paths P1 through PN. The patient telemetry device may comprise a known device capable of monitoring patient data, transmitting that data to the central server and, optionally, receiving data from the central server 200.

The central server 200 examines the communicated data to determine if the at least one physiological parameter is within appropriate or "normal" parameter boundaries. If the data is not within the appropriate boundary, the central server 200 determines if an event or medical anomaly (e.g., cardiac arrest or other condition) may be occurring. If such a determination is made, then the central server 200 communicates an offer to one or more of the physician terminal devices via respective data paths E1 through EN.

Each physician terminal device 110 (i.e., physician terminals 110-1 through 110-N) is associated with at least one respective expert, such as physician(s), nurse(s), and other experts. A physician receiving an offer accepts that offer by communicating an acceptance message to the central server 200 via the physician terminal device 110 or another means (e.g., telephone, computer network and the like). The central server then decides which one (or more than one) of the accepted offers will be confirmed by sending a confirmation signal to the physician via, e.g., the respective physician terminal device(s). The physician terminal device may comprise a known device capable of receiving information from the central server and, optionally, transmitting information to the central server 200. For example, a pager, a personal digital assistant (PDA) or a cellular telephone may be utilized for this purpose.

An exemplary embodiment of a patient telemetry device 120-1 comprises an input/output (I/O) circuit 125, support circuitry 123, a processor 124, a memory 126 and a data link 127. The processor 124 cooperates with conventional support circuitry 123 such as power supplies, clock circuits, cache memory and the like as well as circuits that assist in executing the various software routines within the patient telemetry device 120-1. Input/output circuit 125 forms an interface between the patient telemetry device 120 and sources of patient physiological data. For example, the input/output circuit 125 may comprise sensors, transducers and other analog to digital conversion circuitry adapted to measure physiological parameters associated with a patient, such as heart rate, blood pressure, temperature, perspiration level, respiratory activity, body electrical activity, brain activity and the like. The physiological information is received and/or processed by the input/output circuitry to produce physiological parameter representative data in a form usable by processor 124. The processor 124 communicates the physiological parameter representative data to the central server 200 via a data link 127.

Data link 127 comprises a wireless or a non-wireless data link (e.g., a telephone dialer, a cellular telephone link, or a computer link) or other communications link driver suitable for providing patient data to the central server 200, via a respective data path (e.g., data path P1). The patient telemetry device is optionally responsive to a patient control signal. The patient control signal comprises a signal that a patient may use to communicate specific information or a request to the central server 200. For example, in the case of a patient sensing the onset of some physiological anomaly (e.g., the beginning of cardiac arrest) or the patient suffering a trauma (such as a fall), the patient may manually communicate this condition to the central server 200 such that appropriate action (e.g., summon an ambulance) is taken. The patient control signal is produced by an optional input device 145, illustratively, a key pad. The patient control signal is used to communicate a message to the central server 200 comprising, e.g., a standby mode message, an impending exertion message, an equipment failure message, a medical emergency message, a non-medical emergency message, a specific physiological dysfunction message and a test message. In response to such a message, the system may choose to ignore any apparent anomalies.

An exemplary embodiment of a physician terminal device 110-1 comprises an input/output (I/O) circuit 115, support circuitry 113, a processor 114, memory 116, a display device 111 and a data entry device 112. The processor 114 cooperates with conventional support circuitry 113 such as power supplies, clock circuits, cache memory and the like as well as circuits that assist in executing various software routines. The physician terminal device 110-1 also contains input/output circuitry 115 that forms an interface between the physician terminal device 110 and the central server 200. The display device 111 comprises a liquid, crystal display (LCD) or other display means, while the data entry device 112 comprises a keyboard or other data entry means. The memory 116 includes a standard control program such as a PDA or cellular telephone control program that enables a physician or expert interacting with the physician terminal device to receive information from the central server 200 and, optionally, transmit information back to the central server 200.

Referring now to the patient telemetry device 120-1, in one embodiment of the invention, the physiological information received from the patient is merely converted into a digital information stream, either compressed or uncompressed, and transmitted directly to the central server 200. That is, the patient telemetry device does not perform any analysis of the physiological data. The data is merely passed to the central server 200 in either a compressed or uncompressed data format as appropriate to, e.g., the format of data link P1. Compressed data transfer may be effected using various compression methods, such as the frequency domain transform functions utilized in known communications systems.

In another embodiment of the invention, the processor 124 performs an analysis of the received physiological information to determine if, for example, monitored parameters of the patient are within appropriate boundaries. For example, the processor 124 may be programmed (via a control program within the memory 126) to issue an alert to the central server 200 in the event of a patient heart rate exceeding an upper threshold level or dropping below a lower threshold level. Multiple parameter alarms may be programmed such that particular combinations of physiological parameter levels trigger specific alerts indicative of specific conditions.

In another embodiment of the invention, the patient telemetry device 120-1 and central server 200 communicate bi-directionally. In this embodiment, parameter threshold levels are optionally updated via the data link (P1-PN) or other means (e.g., via an internet or telephone connection) such that patient monitoring may be calibrated to the changing needs of a patient. For example, if a patient is about to exercise, it is quite likely that the measured heart rate will increase. Therefore, the patient may communicate this fact to the central server 200 via a patient control signal produced using the key pad 145. Bi-directional communication may be effected via the internet 170 or other communications medium.

In another embodiment of the present invention utilizing bi-directional communication with the central server 200, the patient telemetry device 120-1 is associated with a drug dispensing device 130. In this embodiment of the invention, the central server 200 may be used to control the dispensing of drugs to the patient via the drug dispensing device 130. For example, in the case of a patient exhibiting physiological information indicative of cardiac arrest, the central server 200 may cause the drug dispensing device 130 to dispense medication tending to reduce or mitigate any harm to the patient due to the event. In the case of local analysis by the patient telemetry device 120, the decision to dispense medication may be made locally. Additionally, medication dispensing may be placed under the control of the patient (e.g., pain medication up to a predefined dosage rate). Optionally, the local control of medication dispensing is communicated to the central server 200 where the patient's medical records are responsively updated.

In another embodiment of the present invention utilizing bi-directional communication with the central server 200, the patient telemetry device 120 is associated with a global positioning system (GPS) locator 135. The GPS locator 135 comprises known GPS receiver circuitry suitable for determining the geographic position of the patient (assuming the patient is near the GPS locator). The geographic position of the patient is transmitted to the central server 200 for use in, e.g., directing an ambulance to the patient, performing geographical-based analysis of aggregated patient data or other functions.

In another embodiment of the invention utilizing bi-directional communication with the central server 200, the patient telemetry device 120 is associated with an automatic external defibrillator (AED) 140. In the event of the physiological information of the patient being indicative of, e.g., a ventricular fibrillation, a central server or decision may indicate that defibrillator is appropriate. In this case, the central server or patient telemetry device causes the automatic external defibrillator to enter an active mode of operation. Present automatic external defibrillators include monitoring capabilities such that they do not administer an electric shock to a patient unless such an electric shock is warranted. That is, present automatic external defibrillators perform monitoring operations to confirm the need for a defibrillator. Such functionality may optionally be incorporated into the patient telemetry device 120.

In another embodiment of the invention, a security system 150 associated with the patient is coupled to the patient telemetry device 120 such that in the event of a medical emergency, the central server 200 is contacted and, additionally, a security system server (not shown) is also contacted. In this embodiment of the invention, where a patient is paying a monitoring fee to a security system service, the data link 127 may communicate to the central server 200 via the security system 150 rather than the data link 127 (e.g., telephone lines, cellular telephone, two-way paging and the like).

In another embodiment of the invention, a medical records clearing- house 180 is used to store patient medical records. In this embodiment of the invention, the patient medical records are communicated to a confirmed expert (i.e., a physician accepting an offer that has been subsequently confirmed) via the internet 170 or via the central server 200.

Figure 2:
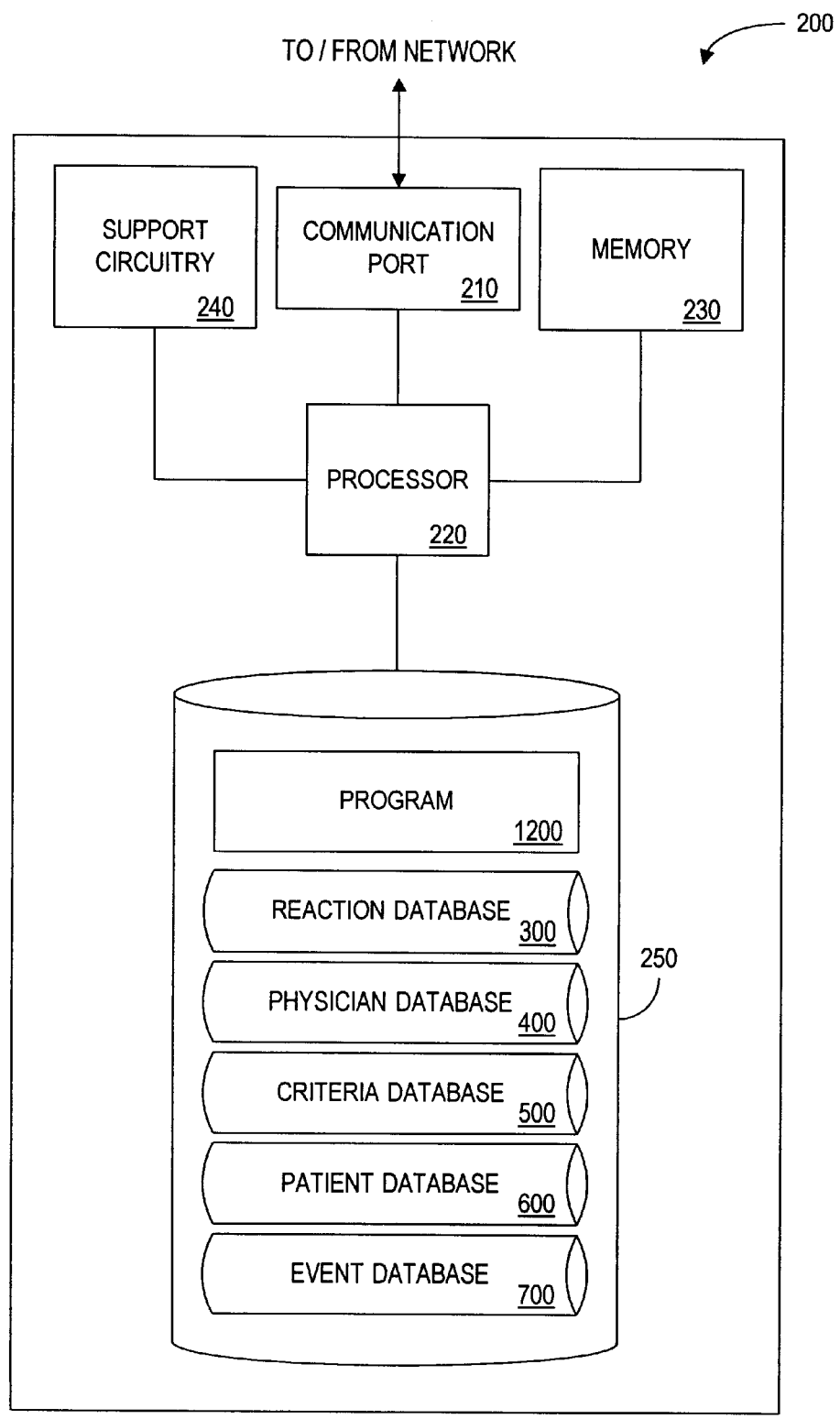
FIG. 2 depicts a high level block diagram of a central server 200 suitable for use in the patient care diagnosis delivery system of FIG. 1.

FIG. 2 depicts a high level block diagram of a central server 200 suitable for use in the patient care diagnosis delivery system of FIG. 1. Specifically, the central server 200 of FIG. 2 comprises a communications port 210, a processor 220, a memory 230, support circuitry 240 and a storage device 250. The communication port 210 forms an interface between the central server 200 and the physician terminal devices 110-1 through 110-N, the patient telemetry devices 120-1 through 120-N and, optionally, the internet 170 and the medical records clearinghouse 180. The processor 220 cooperates with support circuitry 240 and memory 230 to run various programs 1200 and use various databases 300–700 stored in storage device 250. Specifically, the storage device 250 is used to store a program 1200 that will direct the processor 220 to perform the methods of the present invention and to store various databases 300–700 used to implement the methods of the present invention. In an exemplary embodiment, the storage device 250 is used to store a reaction database 300, a physician database 400, a criteria database 500, a patient database 600 and an event database 700. The reaction database 300 will be discussed in more detail below with respect to FIG. 3, the physician database 400 will be discussed with more detail below with respect to FIG. 4, the criteria database 500 will be discussed in more detail below with respect to FIGS. 5A and 5B, the patient database 600 will be discussed in more detail below with respect to FIG. 6 and the event database 700 will be discussed in more detail below with respect to FIG. 7. It should be noted that the programs and databases may be stored locally in the central server 200 or in a remote location, such as the optional medical records clearing house 180 depicted in FIG. 1.

The operation of the central server 200 will be described in more detail below with respect to FIGS. 8–12. Briefly, in one embodiment of the invention the central server 200 receives a continuous signal from each patient; the received signal is analyzed to determine if any predefined patterns or data aberrations exist; any such patterns or data aberrations are further analyzed to determine whether the pattern or data aberration is pathological; if pathological, then the central server 200 searches the physician database for an expert, such as a physician, appropriate to the treatment of patients exhibiting such pattern or data aberration and, if appropriate, an ambulance is dispatched to bring the patient to a hospital; the expert is then paged and offered compensation to render an expert diagnosis on the patient's condition; in the case of an expert accepting the offer, the central server 200 confirms the acceptance and transmits to the expert a copy of at least a portion of the patient's medical history and a description of the current pattern or data aberration so that the expert diagnosis may be rendered.

FIG. 3 depicts table 305, exemplary of reaction database 300, suitable for use in the central server of FIGS. 1 and 2. Specifically, the table 305 of FIG. 3 comprises a plurality of records R31 through R36, each record being associated with a respective alert field 310 and a respective system reaction field 320. The alert field 310 of a record indicates a specific alert condition. The system reaction field 320 of the record indicates an appropriate system reaction to the corresponding alert field 310 of the record.

It is noted that the alert fields 310 of the table 305 of FIG. 3 assume that the patient telemetry devices 120 of the system 100 of FIG. 1 provide alert information to the central server 200. That is, the patient telemetry devices 120-1 through 120-N perform a local data analysis (or receive direct patient input) and responsively issue an alert code to the central server. The table 305 provides, for each predefined alert, an appropriate system response to the alert. Additionally, the table 305 of FIG. 3 is shown with only six records (R31 through R36). However, it will be appreciated by those skilled in the art that the reaction database 300 may comprise an unlimited number of records.

Alert field 310 of records R31 through R36 is depicted as indicating alert conditions as follows: ventricular fibrillation R31; loss of consciousness R32; aberrant blood glucose levels R33; fetal heart monitor alarm R34; tachycardia R35; and acutely high blood pressure R36.

System reaction field 320 of records R31 through R36 is depicted as indicating the following system responses to corresponding alert conditions as follows: summon an ambulance and offer the case to one or more cardiologists R31; summon an ambulance and offer the case to an emergency room physician R32; instruct the patient to take insulin and, if the blood glucose levels do not return to normal after a predefined period of time (e.g., 15 minutes,) offer the case to one or more nurses R33; alert the mother, instruct her to go to the hospital and offer the case to one or more obstetricians R34; offer the case to one or more cardiologists and query the patient as to the patient's present activity level (e.g., was patient climbing stairs, playing basketball, watching television and the like) R35; and offer the case to one or more internists and query the patient as to a present activity level R36.

FIG. 4 depicts table 405, exemplary of physician database 400 suitable for use in the central server of FIGS. 1 and 2. Specifically, the table 405 of FIG. 4 comprises a plurality of records R41 through R49, each record being associated with a respective physician's name field 410, a physician identifier field 420, a physician criteria codes field 430, a specialty field 440, a previous case identifiers field 450, an availability field 460 and a contact information field 470. It should be noted that the availability field 460 may provide conditional information, i.e., an unavailable physician will always be available if a compensation level exceeds a threshold amount such as illustrated in record R48.

For each record, the physician's name field 410 indicates the name of a particular physician; the physician identifier field 420 indicates an insurance company, hospital or other identification number or code that uniquely identifies the physician; the physician criterion codes field 430 indicates physician criterion information (e.g., fee structure, board certification and the like); the specialty field 440 indicates the physician's specialty (e.g., Cardiology, Surgery and the like); the previous case identifiers field 450 indicates the case identifiers of previous cases handled by the physician; the availability field 460 indicates whether the physician is presently available to handle a case; and the contact information field 470 indicates the preferred method of contacting the physician, e.g., voice, pager, email and the like. Physicians indicate their availability by, for example, logging onto a web site or otherwise communicating by alternate means with to the system to inform the system when they become available and when they cease to be available.

Record R41 of table 405 indicates that a physician named John Doe has a corresponding identifier "123456", criterion codes "UH", "BS", "M33" and "MW", a specialty of "Emergency Medicine", previous case identifiers of "C987654", "C876543" and "C765432", an availability indication of "yes" and contact information indicative of a pager number of 555-1234. Record R42 indicates that a physician named Bob Smith has a corresponding identifier "234567", criterion codes "UH", "M33" and "MW", a specialty of Cardiology, previous case identifiers of "C654321", "C543210" and "C432109", an availability indication of "no" and contact information indicative of a voice number of 555-2345.

Records R43 through R49 contain similar data regarding other physicians. The physician criterion codes field 430 will be discussed in more detail below with respect to FIG. 5A. For example, Record R48 of table 405 indicates that a physician named Alex Schwartz has a corresponding identifier "8980123", criterion codes "UH", "BS", "BC" and "MP", a specialty of "Endocrinology", previous case identifiers of "C999876" and "C888765", an availability indication of "only above $150" (i.e., only available of offer is at least $150) and contact information indicative of an email address of good_doc@hospital.com. The previous case identifier field 450 will be discussed in more detail below with respect to FIG. 7.

FIG. 5A depicts table 500A, exemplary of one embodiment of criteria database 500A suitable for use in the central server of FIGS. 1 and 2. Specifically, the table 500A of FIG. 5A comprises a plurality of records RA51 through RA58, each record being associated with a respective physician criterion field 510 and a physician criterion code field 520.

For each record RA51 through RA58, the physician criterion field 510 indicates a particular objective or subjective criterion that may be applied to a physician. Subjective physician criteria comprises subjective preferences of the physician (e.g., preferred patients, insurance plans, hospitals and the like). For each record RA51 through RA58 the physician criterion code field 520 contains the corresponding code, or abbreviation, of the objective or subjective criterion contained within the respective physician criterion field 510. If a criterion is applicable to a given physician, the code for that criterion will appear in the physician criterion codes field 430 of a record associated with that physician in the physician database 400.

The contents of the physician criterion field 510 and the physician criterion code field 520 of records RA51 through RA58 are as follows: a physician criterion of universal health approved physician criterion is associated with code UH (record RA51); Blue Shield approved physician criterion is associated with code BS (record RA52); board certified physician criterion is associated with code BC (record RA53); fee structure in upper $33^{rd}$ percentile criterion is associated with code U33 (record RA54); fee structure in middle $33_{rd}$ percentile criterion is associated with code M33 (record RA55); fee structure in lower $33^{rd}$ percentile criterion is associated with code L33 (record RA56); male physician criterion is associated with code ND (record RA57) and female physician criterion is associated with code FP (record RA58).

FIG. 5B depicts a table 500B, exemplary of another embodiment of criteria database 500 suitable for use in the central server 200 of FIGS. 1 and 2. Specifically, table 500B of FIG. 5B comprises a plurality of records RB51 through RB514, each record being associated with a respective patient criterion field 530 and a patient criterion code field 540.

For each record, the patient criterion field 530 indicates a particular objective or subjective criterion applied to a physician treating a patient that is required or preferred by the patient or the patient's insurance provider. Subjective criteria comprises subjective preferences of the patient (e.g., preferred physicians, preferred hospitals and the like). The patient criterion code field 540 of a record contains the code, or abbreviation, of the objective criterion contained within the respective patient criterion field 530. A physician having a criterion code contrary to a required patient criterion code is deemed to be undesirable to the patient. A physician having all criterion codes matching those of the patient is deemed to be most desirable to the patient. Physicians having some criterion codes matching the patient preferred criterion codes may be ranked in order of preference according to the amount of correlation between the patient's and physicians' criterion codes.

The contents of the patient criterion field 530 and the patient criterion code field 540 of records RB51 through RB514 are as follows: require universal health approved physician criterion is associated with code R-UH (record RB51); prefer universal health approved physician criterion is associated with code P-UH (record RB52); require Blue Shield approved physician criterion is associated with code R-BS (record RB53); prefer Blue Shield approved physician criterion is associated with code P-BS (record RB54); prefer fee structure in upper $33^{rd}$ percentile criterion is associated with code P-U33 (record RB55); prefer fee structure in middle $33^{rd}$ percentile criterion is associated with code P-N33 (record RB56); prefer fee structure and lower $33^{rd}$ percentile criterion is associated with code P-L33 (record RB57); require board certification criterion is associated with code R-BC (record RB58); prefer board certification criterion is associated with code P-BC (record RB59); require male physician criterion is associated with code R-MP (record RB510); prefer male physician criterion is associated with code P-MP. (record RB511); require female physician criterion is associated with patient code R-FP (record RB512); prefer female physician criterion is associated with code P-FP (record RB513) and require first available physician criterion is associated with criterion code R-FA (record RB514).

FIG. 6 depicts a tabular representation 605 of an exemplary patient database 600 suitable for use in the central server 200 of FIGS. 1 and 2. Specifically, the table 605 of FIG. 6 comprises a plurality of records R61 through R68, each record being associated with a respective patient's name field 610, patient identifier field 620, patient criterion code field 630, a "currently being treated for" field 640 and a past alerts field 650.

For each record R61 through R68, the patient's name field 610 indicates the name of a particular patient; the patient identifier field 620 indicates an insurance company, hospital or other identification number or code that uniquely identifies the patient; the patient criterion codes field 630 indicates patient criterion information relating to preferred objective or subjective characteristics of a treating physician (e.g., fee structure, board certification and the like); the currently being treated for field 640 indicates the current medical conditions (if any) that the patient is currently being treated for and the past alerts field 650 indicates the medical conditions (or general health) that triggered previous alerts or other events.

A number of exemplary patient criteria appear in this database. The codes for patient criteria correspond to those for physician criteria, except that patient codes have either an "R" or "P" prefix. For example, the code for a board-certified physician is BC; the patient codes for board-certified physicians are R-BC and P-BC. Patient criterion codes with "R" prefixes indicate that the patient requires the criterion corresponding to this code. Patient criterion codes with "P" prefixes indicate that the patient prefers but does not require this criterion. Some patient criteria, such as requiring the response of the first available physician, do not have corresponding physician criteria codes.

Entries in the patient criterion codes field 630 may be determined not only by the patient, but, optionally, by the patient's family physician, insurance company or other entity. The currently being treated for field 640 contains brief information about the patient's current medical conditions. A "general health" entry in this field indicates that the patient is not currently being treated for anything in particular, but is instead being monitored just in case any problems develop. In one embodiment of the invention, a patient's medical records are sent to a physician by providing the physician with a hyperlink or data path, such that the physician can access the files directly from a computer terminal connected to the internet or other computer network.

Record R66 of table 605 indicates that a patient Matt Smith is associated with an identifier number "678901", criteria codes P-MP, P-U33 and P-BC, is currently being treated for "general health" (i.e., no particularized ailment) and lost consciousness during a past alert on Jan. 1, 1998. Record R67 of table 605 indicates that a patient Teun Van Vliet is associated with an identifier "789012", criteria codes R-UH and P-L33, is currently being treated for "Arteriosclerosis" and has never been associated with an alert. Record R68 of table 605 indicates that a patient Ana Ng is associated with an identifier "890123", criteria codes R-BS, P-BC and R-FP, is currently being treated for "Possible Pregnancy Complications" and has never been associated with an alert. Records R61 through R65 contain respective data relating to other patients.

FIG. 7 depicts a table 705, exemplary of event database 700, suitable for use in the central server of FIGS. 1 and 2. Specifically, the table 705 of FIG. 7 comprises a plurality of records R71 through R74, each record being associated with a respective date field 710, case identifier field 720, patient identifier field 730, physician identifier field 740, event description field 750, outcome field 760, offers made field 770 and offers accepted field 780. The offers made field 770 and offers accepted field 780 include respective physician identifiers and compensation value offered subfields.

The date field 710 indicates the date of a particular event. The case identifier field 720 identifies, by a unique case identifier, the particular event. The patient identifier field 730 and physician identifier field 740 identify, respectively, the patient and physician involved in the event. The event description field 750 includes a description of the event. The outcome field 760 includes information defining the outcome of the event (e.g., the patient was admitted to a hospital, treated in a particular manner, administered a certain drug and the like). The offers made field 770 include information identifying each physician to whom an offer of compensation in exchange for diagnostic services was made, and the amount of money offered for such services. The offers accepted field 780 includes information indicating which physician or physicians accepted the offer and at what compensation value they accepted the offer. Optionally, a "past alerts" field contains a record of previous alerts and is used to ascertain whether certain patients (or devices) are prone to false alarm events.

The offers made field 770 and offers accepted field 780 are optionally used to improve the system accuracy in predicting physician demand and prices. For example, the system may determine that physician "596143", an internist, regularly accepts offers $50 below the median offer for internists. In this scenario, offers to this physician may be reduced. By graphing acceptance rate against offer values, time of day and other factors, the system continually absorbs information relating to the contracting behavior of physicians, thereby refining estimates of demand and appropriate prices.

Record R71 of table 705 indicates that on Jan. 1, 1998 a case "678901 A" involving a patient "678901" and a physician "123456" involved a loss of consciousness. A first physician "0123456" was offered $180, a second physician "789012" was offered $200 and a third physician "406961" was offered $220 to accept the case. The first physician "123456" and the second physician "789012" accepted the case at the offered amount. The event resulted in an admission to a hospital for a narcotics overdose.

Record R72 of Table 705 indicates that on Jan. 11, 1998 a case "505995A" involving patient "505995" and physician "567890" involved an event of acute high blood pressure and had an outcome of the patient being queried and found him to be exercising. A physician identified as "234567" was offered $375, a second physician identified as "567890" was offered $375 and a third physician identified as "961642" was offered $385 to take the case. The first and third physicians accepted the offers at the offer price.

Record R73 of Table 705 indicates that on Feb. 14, 1998 case "381884A" involving patient "381884" and physicians "567890" and "234567" involved a tachycardia event with an outcome of hospital admission for the patient. Physician "567890" was offered $350 and physician 234567 was offered $375 for taking the case. Both physicians accepted the offer at the respective offer price.

Record R74 of Table 705 indicates that on Mar. 15, 1998 case "567890A" involving patient "567890" and physician "234567" involved an event of acute high blood pressure and resulted in an emergency room administration of appropriate drugs and a release of the patient. A first physician "234567" was offered $350 and a second physician "567890" was offered $375 for taking the case. The first physician "234567" was subsequently offered $375 and then $400 for taking the case. Physician "234567" finally accepted the $400 offer price.

Figure 8A:
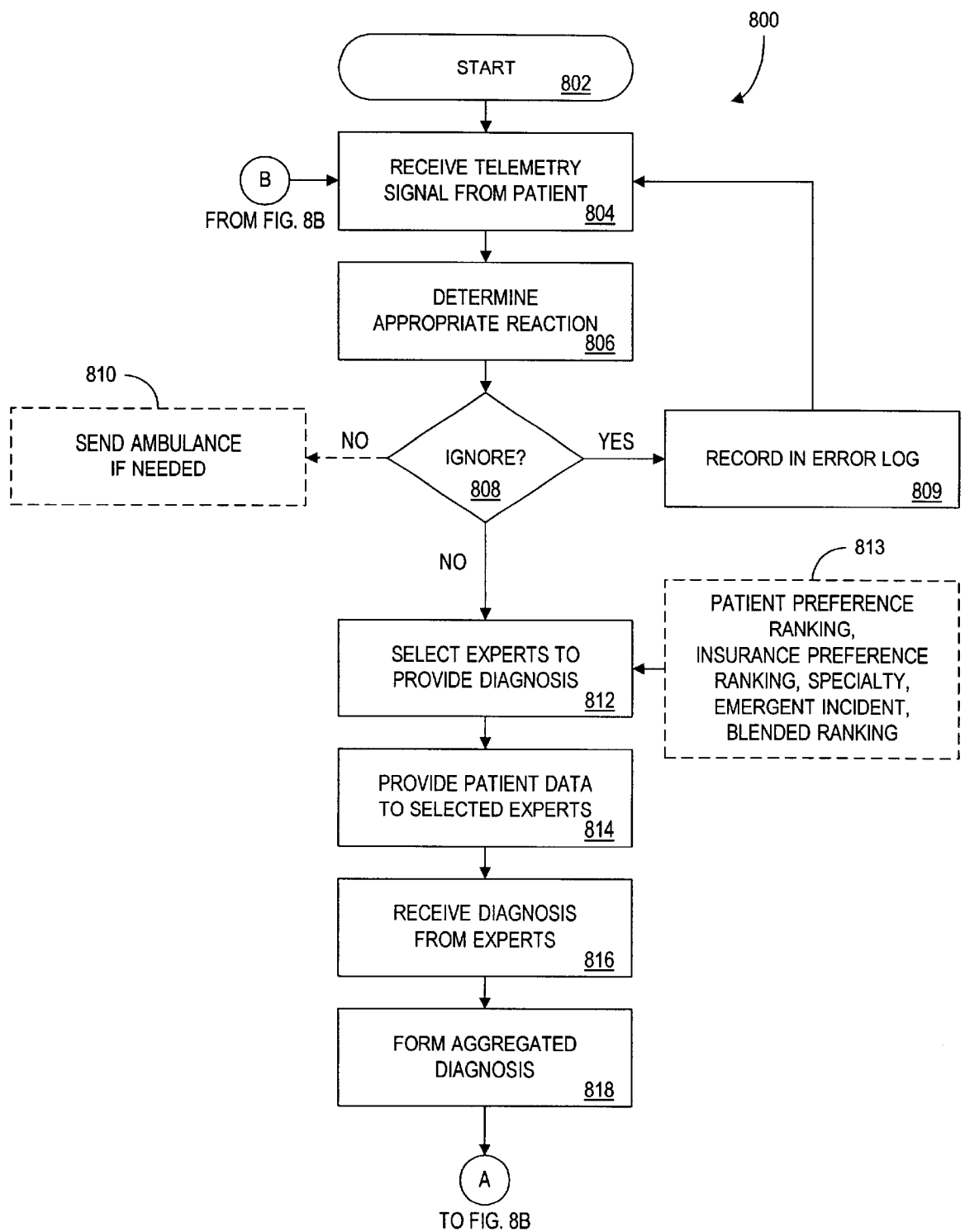
FIGS. 8A and 8B depict a flow diagram of a patient care diagnosis delivery method suitable for use in the patient care diagnosis delivery system of FIG. 1.
Figure 8B:
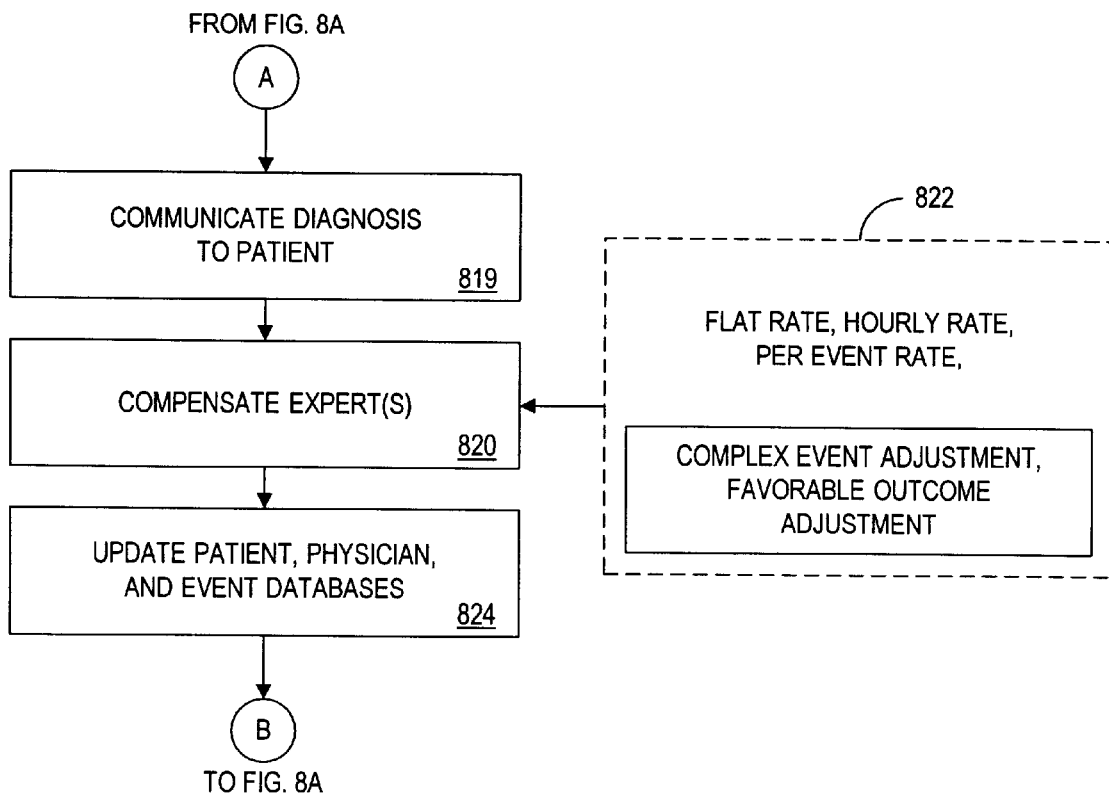

FIGS. 8A and 8B depict depicts a flow diagram of a patient care diagnosis delivery method suitable for use in the patient care diagnosis delivery system of FIG. 1. Specifically, the patient care diagnosis delivery method 800 of FIGS. 8A and 8B is suitable for use within the central server 200 of the patient care diagnosis delivery system 100 of FIGS. 1 and FIG. 2.

The method 800 is initiated at step 802. At step 804 a telemetry signal is received from a patient. As previously noted with respect to FIG. 1, the telemetry signal may comprise compressed or uncompressed physiological data without local analysis, compressed or uncompressed physiological data with a local analysis (i.e., including an alarm code), a control signal produced by the patient and, optionally, other data.

At step 806 a determination is made as to the appropriate reaction of the patient care diagnosis delivery system 100. In the case of compressed or uncompressed physiological data without local analysis, the data is analyzed to determine if patterns within the data are indicative of a present or pending (i.e., precursor indications of dysfunction) physiological dysfunction. This analysis may be conducted using one or more of a number of known data analysis techniques. In the exemplary embodiment, the analysis is conducted by comparing portions of the data to data profiles that have been determined to be indicative of such present or precursor physiological dysfunction. In the case of compressed or uncompressed physiological data with local analysis (e.g., alarm codes), the received alarm code is compared to the alert field 310 of the records within the reaction database 300. A favorable comparison to a record yields, from the system reaction field 320 of that record, the appropriate response to the received alarm code. It should be noted that the data profiles may be periodically updated or altered.

In the case of compressed data that has been compressed using a frequency transform compression scheme, the step of comparing the compressed data may be performed within the compressed data domain (i.e., frequency domain) by performing the following steps: transforming, using a frequency domain transform function, the data representative of the physiological parameter; and correlating, against each of a plurality of frequency domain profiles, the transformed data representative of the physiological parameter, where each of the frequency domain profiles is associated with at least one pathological anomaly.

A control signal produced by the patient is also reacted to in a predefined manner based upon the signal. For example, a control signal indicative of pending patient exercise indicates to the central server 200 that a subsequent increase in blood pressure is to be expected, though the system will still react appropriately to data indicative of cardiac arrest.

At step 808 a query is made as to whether the determination at step 806 indicates that the received telemetry signal should be ignored. If the query at step 808 is answered affirmatively (e.g., elevated blood pressure during exercise), then the method proceeds to step 809 where, optionally, an entry in an error log (not shown) is made and the method proceeds to step 804 where the next telemetry signal is received. If the query at step 808 is answered negatively, then the method 800 proceeds to step 812. Optionally, if the query at step 808 is answered negatively, then the method 800 proceeds to step 810, where an ambulance is dispatched to the patient's location, if needed. The patient's location may be determined with respect to a known location or, in the case of a patient telemetry device 120 associated with a GPS locator 135, GPS data within the received signal will provide location information.

At step 812 one or more experts are selected to provide diagnostic services. The expert(s) selected to provide such services are selected based upon the physician criterion 500A of FIGS. 5A and patient criterion 500B of FIG. 5B, as will be discussed in more detail below with respect to FIGS. 9A and 9B.

Briefly, the above-mentioned criteria result in a patient preference ranking of physicians, as modified by patient insurance company requirements, according to medical specialty, gender, fee structure and the like. Patient preference ranking is based upon a patient criterion within patient criterion database 500B. Physician preference ranking is based upon the physician criterion database 500A. Insurance company preference ranking is based upon insurance company information within either of the patient criterion database 500B or physician criterion database 500A or other database. For example, insurance companies may have negotiated or predefined contractual arrangements with individual physicians, physician groups and/or hospitals or hospital systems. In the case of a preferred hospital system or other medical facility, an insurance company may have preferred providers within that facility and these providers may or may not be reflected in the patient preference rankings. However, since the insurance company associated with a particular patient is likely to be the one paying the bill, it is prudent to adapt the selection of experts to the insurance company preference ranking to the extent possible. The specialty of an expert selected to provide diagnostic information may be dependent upon, e.g., the received telemetry signal from the patient and/or the patient's medical data or history. In the case of an emergency situation or emergent event, it may be necessary to immediately secure some expert opinion, regardless of physician specialty or other preferential ranking. These criteria or other criteria may be combined to produce a combined ranking that may be weighted in a manner tending to favor insurance company preferences, patient preferences, physician preferences and other factors as deemed appropriate.

At step 814 at least a portion of the patient's data is provided to the selected expert or experts. The patient data may comprise, e.g., the received telemetry signal, the patient's medical history and any other data appropriate or necessary to the selected experts in rendering their diagnosis.

At step 816 the diagnoses from the expert or experts is/are received. The 20 method 800 then proceeds to optional step 818, where an aggregated diagnosis is formed using a plurality of diagnoses rendered by a respective plurality of experts. The aggregated diagnosis forms a "most likely" diagnosis that is used to determine an appropriate course of treatment for the patient in one embodiment of the present invention.

After receiving an expert diagnosis (step 816) or forming an aggregated diagnosis (step 818), the method 800 proceeds to step 819, where the diagnosis is communicated to the patient, and to step 820, where the expert or experts providing the diagnosis is compensated. The expert compensation may be based upon one of, per step 822, a flat rate, an hourly rate, and a per event rate. Optionally, the compensation may be based upon the time of day (e.g., higher compensation between 10:00 PM and 8:00 AM) or upon physician availability. Optionally, the compensation may be adjusted in the case of a complex event or an especially favorable outcome. A complex event comprises, e.g., an event implicating several specialties or sub-specialties or otherwise causing the expert being so compensated to devote a significantly higher level of time and/or effort to a particular event. A favorable outcome comprises an especially efficient outcome (either monetarily or physiologically) or other superb outcome based upon, e.g., an especially high level of skill applied to an event by an expert being compensated. In emergent situations, an expert may incur a "lost opportunity" cost by handling the case (i.e., failing to gain a greater compensation for another activity so that an emergency event is properly handled). In such cases an additional compensation may be provided.

At step 824 the patient database 600, physician database 400 and event database 700 is updated. The method 800 then proceeds to step 804 to await the next telemetry signal from a patient It should be noted that the above-described a method 800 is applicable to the situation where many cases are handled at once. That is, where many patients are associated with patient telemetry devices providing a substantially continuous flow of information to the server.

Figure 9A:
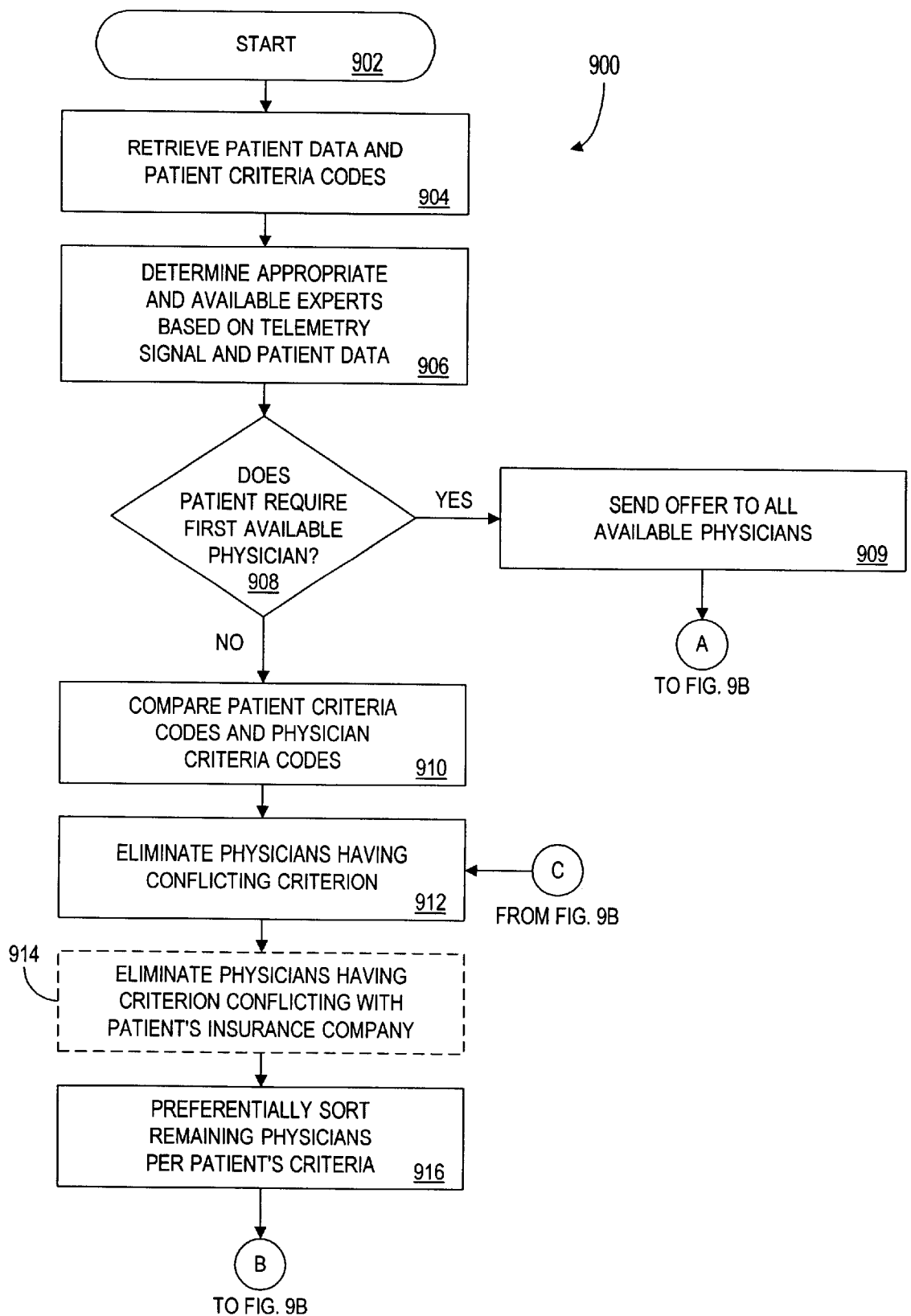
FIGS. 9A and 9B depict a flow diagram of an expert selection method suitable for use in the patient delivery method of FIGS. 8A and 8B.
Figure 9B:
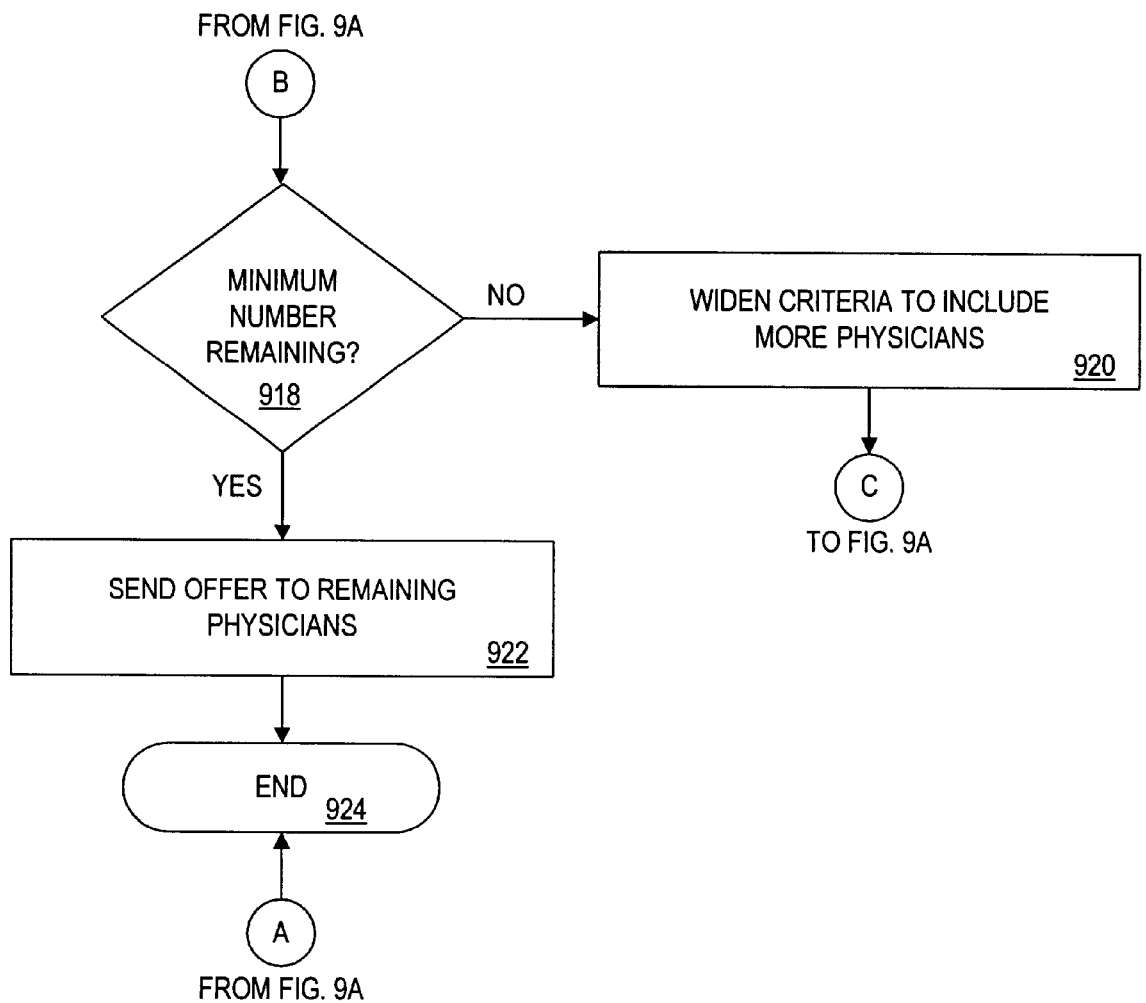

FIGS. 9A and 9B depict a flow diagram of an expert selection method suitable for use in the patient care delivery method of FIGS. 8A and 8B. Specifically, the expert selection method 900 of FIGS. 9A and 9B is suitable for use in implementing, e.g., step 812 of the patient care delivery method 800 of FIGS. 8A and 8B.

The expert selection method 900 is initiated at step 902 and proceeds to step 904. At step 904 patient data and patient criteria codes for the patient transmitting the telemetry signal received at step 804 are retrieved from, respectively, patient database 600 and patient criteria database 500B.

At step 906 a determination is made as to the appropriate and available experts based upon the received telemetry signal and the retrieved patient data. Specifically, the determination made at step 806 is used to define which expertise or specialty is required to render a diagnosis for the event. Additionally, having determined which expert specialty is required, the physician database 400 is accessed to determine which physicians associated with the appropriate specialty are available (per availability field 460).

At step 908 a query is made as to whether the patient requires that a first available physician be contacted (a code R-FA in the patient criteria code field 630 of the patient's record in the patient database 600). Certain alarm codes may also indicate to the system that a first available physician is to be contacted. A code R-FA indicates that a patient is either medically compromised to such an extent that immediate intervention or at least a diagnosis from a physician is required. Therefore, in view of the immediate need for such a diagnosis from an expert, it is imprudent to perform any sorting or preferential arranging of potential experts. Rather, it is most prudent to simply offer to all appropriate and available physicians the "job" of rendering a diagnosis for this event. If the query at step 908 is answered affirmatively, then the method 900 proceeds to step 909. If the query at step 908 is answered negatively, then the method 900 proceeds to step 910.

At step 909 an offer is sent to all appropriate and available physicians as determined during step 906. That is, each physician or expert having the appropriate expertise to render a diagnosis for the present event is offered the chance to render such a diagnosis in exchange for compensation. The method 900 then proceeds to step 924 where it is exited (e.g., the method 800 resumes control at step 814).

At step 910 the patient criteria codes are compared to the physician criteria codes of the appropriate and available experts or physicians. That is, at step 910 a comparison is made between the contents of the appropriate patient criteria code field 540 of the patient criteria database 500B and the physician criterion code field 520 of the physician criteria database 500A to determine if any of the physicians that are appropriate and available have conflicting criterion codes. For example, in the case of a patient criteria code indicative of a requirement for a male physician having a fee structure in the lower $33^{rd}$ percentile, female physicians and those physicians having fee structures in the middle and upper $33^{rd}$ percentile would conflict. At step 912 those physicians having conflicting criterion are eliminated from consideration for an offer of compensation in exchange for diagnostic services. The method 900 then proceeds to optional step 914 or to step 916.

At optional step 914 those physicians having criterion conflicting with the patient's insurance company are eliminated from consideration of receiving an offer of compensation in exchange for their diagnosis. That is, those physicians deemed by the patient's insurance company to be undesirable, too expensive, not included within the health plan or network, in competition with the patient's insurance company's preferred physicians or otherwise deemed unsuitable by the insurance company are eliminated from consideration of an offer (unless later needed, per step 918).

At step 916 those experts and/or physicians determined to be appropriate and available (per step 906) and not eliminated from consideration due to conflicting criterion with a patient (step 912) or insurance company (step 914) criterion list are preferentially sorted per the patient's criteria. That is, those experts still remaining are sorted according to attributes deemed by a patient to be more favorable. For example, in the case of a patient criteria indicative of a preference for a male physician, a preference for a board certified physician, physicians meeting these preferred criteria will be preferentially considered to physicians not meeting these criteria. Thus, the outcome of step 916 is a preferentially sorted list of physicians, physicians near the top of the list are more preferable from the patient's perspective to those physicians near the bottom of the list. This does not mean that the physicians near the bottom of the list are unacceptable; rather that the physicians near the bottom of the list simply fail to meet or to confirm to the patient's criteria as well as those physicians near the top of the list. The method 900 then proceeds to step 918.

At step 918 a query is made as to whether a minimum number of physicians or experts are remaining. That is, a query is made as to whether a predetermined minimum number of physicians are remaining within the pool or group of those physicians under consideration for an offer. The predetermined number may comprise one, three or any appropriate number. In the interest of ensuring that an expert diagnosis is rendered in a timely manner, it may be the case that the predetermined minimum number of physicians being sent an offer at any one time should be low, e.g., five. Thus, if the query at step 918 is answered negatively (e.g., only four physicians in the case of a five physician minimum avoiding elimination for consideration of an offer), then the method 900 proceeds to step 920. If the query at step 918 is answered affirmatively, then the method 900 proceeds to step 922.

At step 920 the criteria of acceptability is widened such that more physicians are included within the list of physicians being considered. For example, the criteria may be widened to include physicians of any gender, regardless of patient preference. The method 900 proceeds from step 920 to step 912.

At step 922 an appropriate respective offer of compensation in exchange for a diagnosis for the particular event triggered by the telemetry signal received at step 804 is sent to each of the remaining physicians. The method 900 then proceeds to step 924 where it is exited (e.g., method 800 is re-entered at step 814).

It should be noted that in the event of no experts indicating an acceptance of their respective offers, additional offers may be transmitted at the same or an enhanced compensation rate to the initial experts selected. Alternatively, some or all of the selected experts are replaced by alternate experts and a new round of offers is made.

Figure 10:
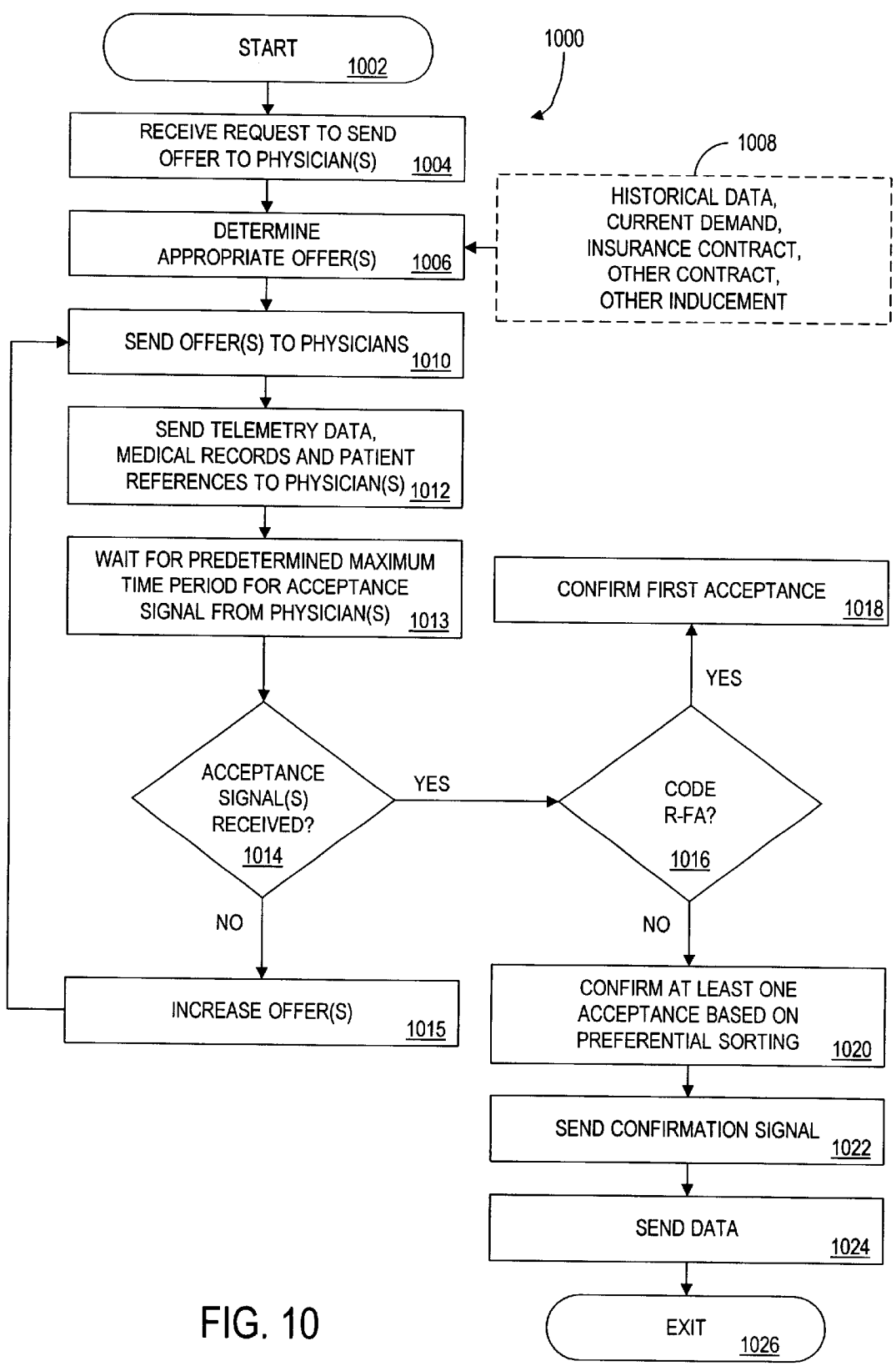
FIG. 10 depicts a flow diagram of an offer processing method suitable for use in the expert selection method of FIGS. 9A and 9B.

FIG. 10 depicts a flow diagram of an offer processing method suitable for use in the expert selection method of FIG. 9. Specifically, FIG. 10 depicts a flow diagram of a method 1000 for processing offer requests or for sending offers to remaining physicians suitable for use in, e.g., step 922 of the expert selection method 900 of FIGS. 9A and 9B.

The offer processing method 1000 is initiated at step 1002 and proceeds to step 1004, where a request to send an offer to one or more physicians is received.

At step 1006 a determination is made as to the appropriate compensation level to be associated with each of the one or more offers to be made to physicians or other experts. An appropriate compensation level may be determined with respect to, per box 1008, historical data, current demand, insurance contracting, other contracts or other inducements.

Historical data comprises data indicative of past offers that have been accepted or rejected by a particular physician. The historical data may be further refined into acceptance and rejection data associated with particular offers on particular days of a month (e.g., weekends or week days) and other historical factors relating to the order acceptance/rejection history of a physician. The offers made field 770 and offers accepted field 780 of the event database 700 provides useful historical data that may be correlated to individual physicians or experts. After determining the appropriate offer levels, the method 1000 then proceeds to step 1010.

Current demand comprises an indicator of an amount of demand for diagnostic services for a particular specialty. For example, during a heat wave compounded by an electrical failure in a city requiring air conditioning it may be the case that current demand for cardiologists and other specialists engaged in the diagnosis and/or treatment of heat-related conditions may be quite high. In this case, such an expert may be extremely busy and more likely to reject an offer to render a diagnosis in the absence of a sufficiently large monetary inducement.

An insurance contract binding a particular physician to the treatment of a patient carrying that insurance at a set contract rate may be honored. Therefore an offer to such a physician may include the appropriate contract compensation rate. However, by prearrangement, a patient availing himself or herself of the system of the present invention may indicate that an additional inducement is to be offered (paid by the patient) to a physician beyond any contract rate negotiated by an insurance company. For example, a person of sufficient means, but insufficient cardiac strength, may offer an additional cash inducement to the hospital or other medical facility or health care provider such that an offer made to a physician should include the insurance contract rate plus the additional cash inducement offered by the patient to arrive at a "bump-up" offer price. Other contractual considerations may include secondary insurance or "gap" insurance in the case of senior citizens or others availing themselves of Medicare and/or Medicaid. In such situations where insurance company contract payments are relatively low, it behooves the patient to increase the level of compensation to some extent such that it is likely a physician will accept the offer of compensation and render the necessary diagnosis.

At step 1010 the respective offers determined at step 1006 are sent to the respective physicians or experts. The method 1000 then proceeds to step 1012.

At step 1012 some or all of the telemetry data, medical records and patient preferences are sent to the physicians or experts receiving offers. The purpose of this data transfer is primarily to provide the expert with sufficient information to make a decision as to whether or not to take the case. However, if all of the patient data is sent, then it is possible that the physician may accept and render an opinion at substantially the same time. The method 1000 then proceeds to step 1013.

At step 1013 the method 1000 waits for a predefined maximum period of time to receive one or more "accept" signals which are received from physicians or experts to whom offers have been sent. That is, a physician may have received an offer via his physician terminal device 110, e.g., a personal digital assistant (PDA) or other portable communication device proximate to the physician. Upon reviewing the offer and, perhaps, some initial patient data, the physician may decide that time allows him or her to render a diagnosis to the patient. In such a situation the physician signals to the central server 200 his or her acceptance of the offer by sending a page or otherwise communicating with the central server 200. For example, upon receiving an offer via a physician terminal device 110, a physician may sit down at a computer terminal and access the server via, e.g., the internet, thereby directly accepting the offer. In the case of a physician accepting an offer via logon to the server using the internet, the dissemination of telemetry data, medical records and patient preferences indicated at step 1012 is performed by the physician downloading this information to his local computing device. Upon receiving at least one "accept" signal within the predefined maximum period of time, or the expiration of that time without receiving an accept signal, the method 1000 proceeds to step 1014.

At step 1014 a query is made as to whether any "accept" signals have been received. If the query is answered affirmatively, then the method 1000 proceeds to step 1016. If the query is answered negatively, then the method 1000 proceeds to step 1015.

At step 1015 the offers are increased. For example, each offer may be increased by a fixed amount (e.g., $25), an amount determined as a percentage (e.g., 15%) of the existing offer or some other amount. It should be noted that an increased offer may be made to less than the entirety of physicians receiving an offer. For example, if one physician is known to typically accept offers above a certain amount, that physician may be provided with a second higher offer, while other physicians may receive second offers having unchanged (or minutely changed) offer amounts. The method 1000 then proceeds to step 1010.

At step 1016 a query is made as to whether the patient associated with the present event is also associated with a code R-FA (requires first available physician). If the query at step 1016 is answered affirmatively, then the method 1000 proceeds to step 1018. If the query at step 1016 is answered negatively, then the method 1000 proceeds to step 1020.

At step 1018, since the patient requires a first available physician, the first acceptance of a physician is confirmed. That is, regardless of patient preferences beyond those already used to screen the physicians to whom offers were made, the first physician indicating his or her acceptance of an offer is confirmed by the central server 200. Confirmation of an offer by the central server 200 entails indicating, in some manner, to the physician that the physicians diagnosis is required, that compensation per the offer will be made for that diagnosis, and that the physician should now be rendering that diagnosis.

At step 1020, since the patient does not require the first available physician, at least one acceptance is confirmed based upon the preferential sorting of the physicians to whom offers were made. That is, in the case of a patient having an insurance company that will pay for the services of one physician to render a diagnosis for an event, the one accepting physician meeting all or most of the patient's preferences will be confirmed as the physician or expert involved in the event. It should be noted that in the case of the patient requiring two or more expert diagnosis to be rendered, the two or more physicians most closely conforming to the patient's preferences as indicated by the patient criterion database 500B will be confirmed.

At step 1022 a confirmation signal is sent to the one or more physicians or experts to be confirmed. The confirmation signal may be sent via the physician terminal device 110 (e.g., pager, cellular or terrestrial telephone link, computer network, satellite network or any other communications medium).

At step 1024 the necessary medical history, current condition and other data associated with the patient and the present event is transmitted to the physician terminal device 110. It should be noted that this step comprises, essentially, the same functionality described above with respect to step 814 of the method 800 of FIGS. 8A and 8A. As such, step 814 may be skipped if the method 1000 of FIG. 10 is being called as, e.g., a sub-method of the method 800 of FIG. 8. The method 1000. then proceeds to step 1026 where it is exited (e.g., the expert selection routine 900 of FIGS. 9A and 9B is reentered at step 924).

Figure 11:
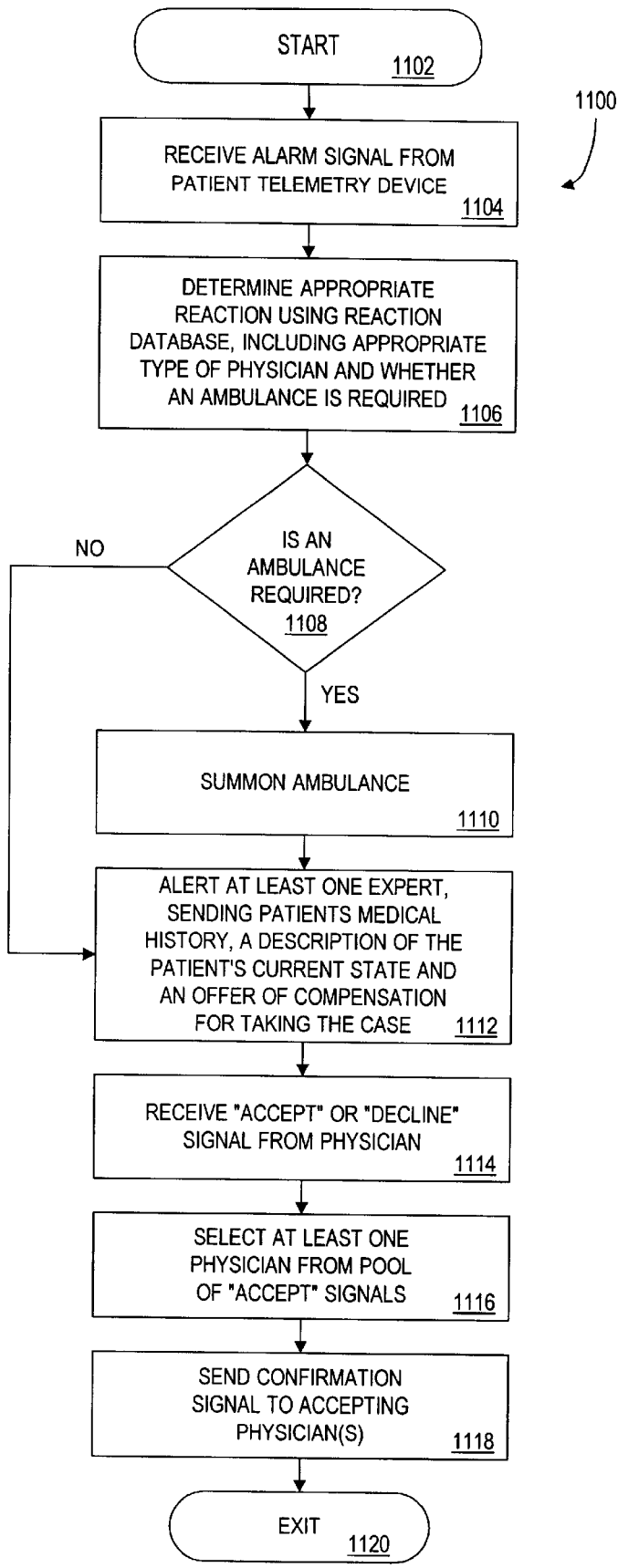
FIG. 11 depicts a flow diagram of a patient care diagnosis delivery method 1100 suitable for use in the patient care diagnosis delivery system 100 of FIG. 1.

FIG. 11 depicts a flow diagram of a patient care diagnosis delivery method 1100 suitable for use in the patient care diagnosis delivery system 100 of FIG. 1. In the embodiment of FIG. 11, the telemetry unit associated with a patient includes at least rudimentary diagnostic capability such that the alarm signal transmitted by the telemetry device includes a particular diagnosis that is associated with an element of the alert field 310 of the reaction database 300 of FIG. 3. For example, in the case of patient telemetry device 120 determining that the patient is suffering ventricular fibrillation, an alert message indicating ventricular fibrillation is transmitted as an alarm signal to the central server 200.

The patient care diagnosis delivery method 1100 is initiated at step 1102 and proceeds to step 1104, where an alarm signal is received from a patient telemetry device. The method 1100 then proceeds to step 1106.

At step 1106 a determination is made as to the appropriate reaction to the alarm signal using the reaction database 300. This determination includes determining an appropriate type of position or expert and whether an ambulance is required. For example, in the case of a received alarm signal indicative of ventricular fibrillation, an appropriate system reaction (per system reaction field 320 or reaction database 300) comprises summoning an ambulance to pick up the patient and bring the patient to a nearby medical treatment facility and offering the case to physicians or experts comprising cardiologists or heart specialists.

At step 1108 a query is made as to whether an ambulance is required. If the query at step 1108 is answered affirmatively, then the method 1100 proceeds to step 1110 where an ambulance is summoned. The method then proceeds to method step 1112. If the query at step 1108 indicates that an ambulance is not required, then the method 1100 proceeds directly to step 1112.

At step 1112 at least one expert is alerted to the event associated with the received alarm, the patient's medical history, a description of the patient's current state and an offer of compensation is then made to the at least one expert in exchange for taking the case (i.e., rendering a diagnosis).

At step 1114 an "accept" or "decline" signal is received from the at least one expert or physician alerted at step 1112. The method 1100 then proceeds to step 1116. At step 1116 at least one of the physicians from the pool or group of physicians or experts indicating an acceptance of the case is selected. The method 1100 then proceeds to step 1118.

At step 1118 a confirmation signal is sent to the accepting expert or experts. At this point the accepting and confirmed physician or expert has taken the case and is expected to render an expert diagnosis using the data transmitted at step 1112 in exchange for the compensation offered at step 1112. The method 1100 then proceeds to step 1120 where it is exited.

Figure 12:
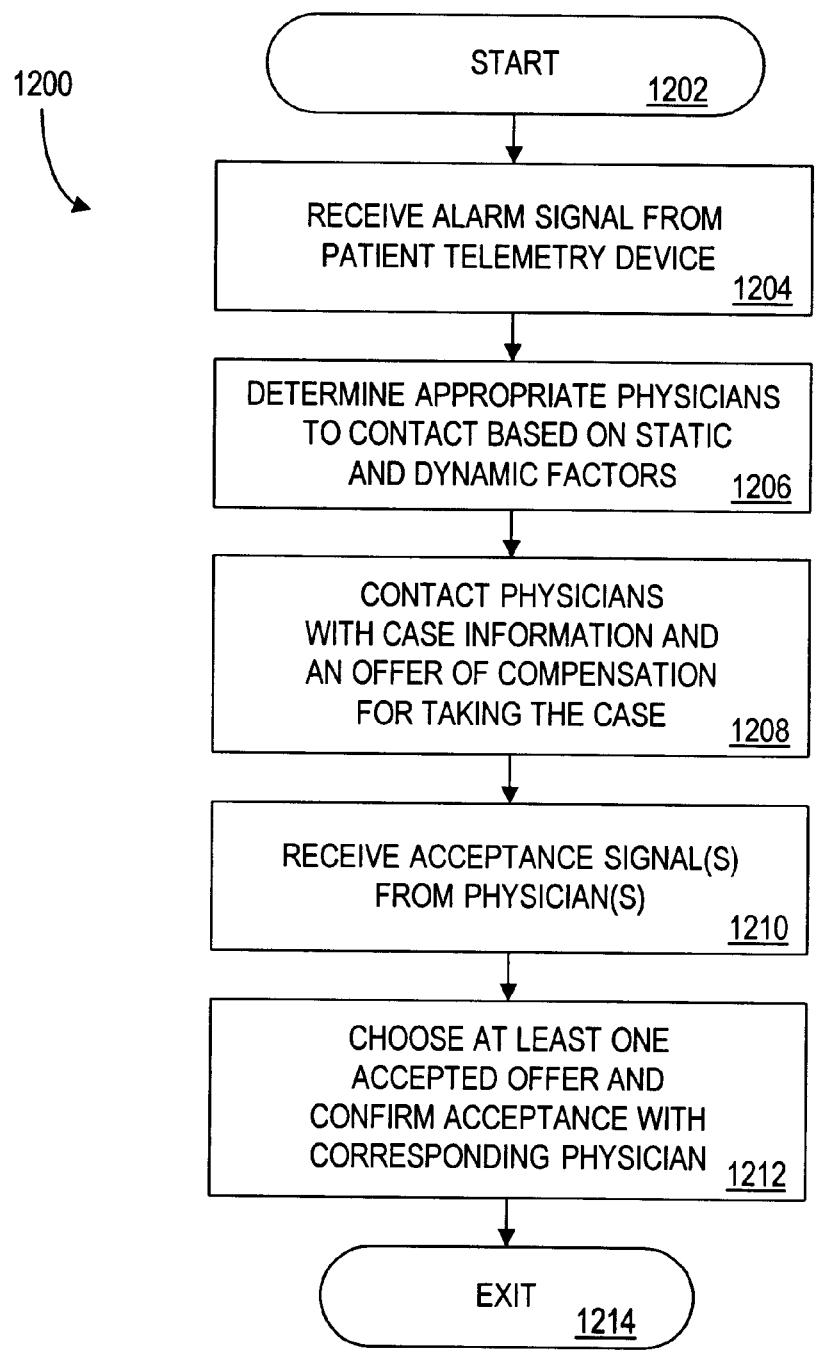
FIG. 12 depicts a flow diagram of a patient care diagnosis delivery method 1200 suitable for use in the patient care diagnosis delivery system 100 of FIG. 1.

FIG. 12 depicts a flow diagram of a patient care diagnosis delivery method suitable for use in the patient care diagnosis delivery system 100 of FIG. 9. Specifically, the patient care diagnosis delivery method 1200 of FIG. 12 is suitable for use within the central server 200 of the patient care diagnosis delivery system 100 of FIGS. 1 and FIG. 2.

The patient care diagnosis delivery method 1200 is initiated at step 1202 and proceeds to step 1204, where an alarm signal is received form a patient telemetry device.

At step 1206 a determination is made as to the appropriate physicians to contact. The determination is made based on static and dynamic factors.

At step 1208 physicians are contacted with case information and an offer of compensation for taking the case.

At step 1210 any acceptance signal(s) is (are) received from the physician(s).

At step 1212 at least one accepted offer is chosen and acceptance of the offer is confirmed with the corresponding physician. The method 1200 then proceeds to step 1214 where it is exited.

An example of an application of the invention will now be described with respect to a cardiac patient. Specifically, it is assumed that the cardiac patient is at a medical facility or at home and that a patient telemetry device monitors the patient physiological parameters including heart activity via, e.g., an electrocardiogram (ECG) function. The ECG continuously monitors the patient's heart and the resulting data is sent to the central server 200 as part of a compressed data stream transmitted via a patient telemetry device 120.

The central server 200 receives the data and analyzes the data to detect any aberrant data patterns, i.e., data patterns indicative of a cardiac anomaly. When such a pattern is detected, the computer compares it with pre-defined malignant patterns (i.e., data profiles) to ascertain whether or not the pattern requires intervention on the part of the patient or the hospital. If the pattern of the received data describes a malignant aberrance such as heart palpitations or arrhythmia, a signal is sent to the patient (to apprise him or her of the situation), and one or more cardiologists are selected to receive an offer according to both patient and physician criteria, as previously described. If a more serious condition were detected, such as a cardiac arrest, the system would summon an ambulance to the patient's location— which could be determined with a GPS unit in the patient telemetry device 120 and also contact a cardiologist. If the pattern observed by the system did not match either a benign or pathological pattern, the system would notify the patient and provide a phone number to call for further assessment of the situation.

The physician terminal device 110 in the example comprises a Personal Digital Assistant (PDA) that is used in conjunction with wireless data transfer. A plurality of experts meeting the appropriate criteria are paged and provided with the patient's current condition, medical records and respective monetary offers. An expert who accepts the case indicates that acceptance via the PDA, which provides two-way paging capability. Depending on the case, the expert communicates with the central server 200 via the PDA, a mobile phone, a computer or some combination thereof. When the expert completed the services required, he or she would indicate this by way of the PDA and a financial account associated with the expert is credited with the amount offered.

If an expert takes too long in responding, the system might make a second or third offer. However, since a large financial risk is associated with the expert attempting to "game" the system (i.e., wait for a, presumably, higher second or third offer), it is likely that the expert will respond quickly if the expert can practicably handle the case. It is noted that, in effect, the plurality of experts receiving offers are in competition with each other. The first (and possibly second) expert accepting the offer will likely exclude from contention the expert trying to elicit a larger second offer.

Advantageously, the invention provides a system that will alert physicians and/or patients when the patient's health takes a turn for the worse. Whether or not a patient lives through a cardiac arrest is often determined by how soon he receives treatment. By cutting the medical response time to the absolute minimum, the inventive system will save lives and reduce impairments to those lives.

In another embodiment of the invention, the expert utilizes the internet to retrieve patient information and render a diagnosis. When contacted with an offer, the expert goes to a web site, types in his expert ID, the patient's ID (received with the offer) and is immediately provided with the patient's records and current condition.

In another embodiment of the invention, the central server 200 sends case offers to hospitals, which then act as clearinghouses for the doctors employed there. For example, the server receives an alarm signal from a monitored patient and sends the offer to one or more hospitals, which then have the option of taking the case, depending on how busy they are. Essentially, the invention operates as a "traffic controller" for hospitals. In this embodiment, a medical facility is associated with at least one expert and comprises infrastructure suitable for remediating physiological dysfunction. The system procures a diagnosis from experts via the facility by transmitting offer(s) to the facility for subsequent communication to the appropriate experts. The facility may adapt the offer (e.g., increase the amount) to ensure that an ambulance delivers a patient to the facility where the physician has admitting rights. The adaptation of the offer may be performed in response to a level of facility utilization and a level of physiological dysfunction urgency associated with said offer. That is, in response to a level of facility utilization being above a threshold level and a level of physiological dysfunction urgency being below a threshold level, the offer may be adapted to cause the patient to be delivered to an alternate or affiliated medical facility for processing.

A plurality of medical facilities may be operably linked together by a central server via a communications system such that the central server, in response to an offer received from a system controller, determines which one of the plurality of medical facilities should receive the offer and communicates the offer to the determined medical facility. Additionally, the determination of the central server may be made using at least one of the following criteria applied to said medical facilities: proximity to a patient, general facility utilization level, appropriate department utilization level (e.g., intensive care unit, trauma unit, emergency room and the like), a level of expertise in treating an indicated physiological dysfunction, possession of equipment suitable for treating the indicated physiological dysfunction, membership in a predetermined health care provider group and participation in a predetermined insurance plan.

In another embodiment of the invention, the invention allows at least voice communication between the remote physician and the patient. The physician gives instructions to the patient on how best to act until an ambulance arrives. If the patient is unconscious, the physician may interact with a bystander to remotely help the patient. Additionally, the physician may optionally administer drugs remotely if a patient telemetry device 110 is equipped with a drug dispensing unit 135.

Although various embodiments which incorporate the teachings of the present invention have been shown and described in detail herein, those skilled in the art can readily devise many other varied embodiments that still incorporate these teachings.

What is claimed is:

1. A method for procuring a diagnosis, comprising the steps of:
   receiving representative data that represents at least one physiological parameter of a patient;
   determining whether the received data is indicative of a physiological anomaly;
   selecting at least one expert to provide an expert opinion regarding the indicated anomaly;
   offering, to said at least one expert, compensation in exchange for providing said expert opinion regarding the indicated anomaly;
   communicating, to the at least one selected expert, the physiological representative data, including the determined anomaly; and
   receiving, from at least one selected expert, a diagnosis of the anomaly.

2. The method of claim 1, wherein the offered compensation comprises a compensation based on one of a fixed compensation amount and a compensation rate.

3. A method for procuring a diagnosis, comprising the steps of:
   receiving representative data that represents at least one physiological parameter of a patient;
   determining whether the received data is indicative of a physiological anomaly;
   selecting at least one expert to provide an expert opinion regarding the indicated anomaly;
   communicating, to the at least one selected expert, the physiological representative data, including the determined anomaly; and
   receiving, from at least one selected expert, a diagnosis of the anomaly,
   wherein said step of selecting comprises the step of: preferentially ranking a group of available experts, wherein said at least one selected expert is selected in accordance with said preferential ranking.

4. A method for procuring a diagnosis, comprising the steps of:
   receiving representative data that represents at least one physiological parameter of a patient;
   determining whether the received data is indicative of a physiological anomaly;
   selecting at least one expert to provide an expert opinion regarding the indicated anomaly;
   communicating, to the at least one selected expert, the physiological representative data, including the determined anomaly; and
   receiving, from at least one selected expert, a diagnosis of the anomaly,
   wherein said step of selecting comprises the steps of:
   selecting at least one expert able to provide a diagnosis of the indicated anomaly;

offering, to the at least one expert, compensation in exchange for providing said diagnosis; and receiving an acceptance of the offer from the at least one expert.

5. A method for procuring a diagnosis, comprising the steps of:

receiving representative data that represents at least one physiological parameter of a patient;

determining whether the received data is indicative of a physiological anomaly;

selecting at least one expert to provide an expert opinion regarding the indicated anomaly;

communicating, to the at least one selected expert, the physiological representative data, including the determined anomaly; and receiving, from at least one selected expert, a diagnosis of the anomaly, wherein said step of selecting comprises the step of transmitting, via respective paging devices, a respective offer to each of said at least one experts.

6. A method for procuring a diagnosis in response to physiological representative data comprising the steps of:

receiving said physiological representative data;

determining if said physiological representative data conforms to a pre-defined data profile indicative of a pathological anomaly;

selecting at least one expert willing to provide medical services tending to remediate said indicated pathological anomaly;

compensating, according to one of a fixed compensation structure or a fee rate, an expert rendering expert services sufficient to diagnose and remediate said indicated pathological anomaly communicating, to said at least one selected expert, information enabling the provision of said medical services to a patient; and receiving from at least one of said at least one selected expert, an opinion providing diagnostic and treatment information.

7. A method for procuring a diagnosis in response to physiological representative data comprising the steps of:

receiving said physiological representative data;

determining if said physiological representative data conforms to a pre-defined data profile indicative of a pathological anomaly;

selecting at least one expert willing to provide medical services tending to remediate said indicated pathological anomaly;

communicating, to said at least one selected expert, information enabling the provision of said medical services to a patient; and receiving, from at least one of said at least one selected expert, an opinion providing diagnostic and treatment information, wherein said step of selecting an expert comprises the steps of:

defining a group of available experts suitable for rendering expert opinion on said indicated pathological anomaly;

sorting said group of experts according to criteria indicative of patient preferences;

communicating, to at least one preferred expert, an offer to render an expert opinion;

confirming, to at least one expert accepting said offer, that said expert shall be compensated per the terms of said offer.

8. The method of claim 7, wherein said step of offering comprises the step of communicating via an electronic communications device.

9. The method of claim 7, wherein said step of selecting comprises the step of confirming a first expert accepting said offer.

10. The method of claim 7, wherein a plurality of said experts accepting said offer is confirmed, and said method further comprises the step of:

aggregating a plurality of expert opinions to form an aggregated opinion.

11. A method for procuring a diagnosis in response to physiological representative data comprising the steps of:

receiving said physiological representative data;

determining if said physiological representative data conforms to a pre-defined data profile indicative of a pathological anomaly;

selecting at least one expert willing to provide medical services tending to remediate said indicated pathological anomaly;

communicating, to said at least one selected expert, information enabling the provision of said medical services to a patient; and receiving, from at least one of said at least one selected expert, an opinion providing diagnostic and treatment information, wherein said step of selecting comprises the steps of:

transmitting an offer to a paging device associated with said expert; and receiving, via a return communication from said expert, an acceptance of said offer.

12. A diagnostic procurement system, comprising:

a monitor, for monitoring at least one parameter associated with an entity and communicating data representing said at least one entity parameter; and a controller, responsive to said data representing said at least one entity parameter, for determining whether anomalous entity operational parameters are present and, in the case of anomalous entity operational parameters being present, procuring a diagnosis from at least one of a predetermined plurality of experts.

13. A diagnostic procurement system, comprising:

a monitor, for monitoring at least one parameter associated with an entity and communicating data representing said at least one entity parameter; and a controller, responsive to said data representing said at least one entity parameter, for determining whether anomalous entity operational parameters are present and, in the case of anomalous entity operational parameters being present, procuring a diagnosis from at least one of a predetermined number of experts, wherein the controller is operable to direct the payment of a fixed compensation in exchange for expert services sufficient to diagnose and remediate said anomalous entity operational parameter.

14. The diagnostic procurement system of claim 12, wherein:

said entity comprises a patient;

said at least one monitored entity parameters comprises physiological information about said patient;

said anomalous entity operational parameters provide information useful in the diagnosis of physiological dysfunction in said patient; and said experts comprise health care professionals.

15. The diagnostic procurement system of claim 12, wherein said controller utilizes said anomalous entity operational parameters to identify precursor conditions indicative of said physiological dysfunction.

16. The diagnostic procurement system of claim 15, wherein said controller utilizes said anomalous entity operational parameters to estimate a time of future occurrence of said physiological dysfunction.

17. The diagnostic procurement system of claim 15, wherein said controller assigns a level of urgency to said indicated physiological dysfunction.

18. The diagnostic procurement system of claim 14, wherein:
said monitor communicates predetermined messages to said controller.

19. The diagnostic procurement system of claim 18, wherein:
said predetermined message comprises at least one of a standby mode message, an impending exertion message, an equipment failure message, a medical emergency message, a non-medical emergency message, a specific physiological dysfunction message and a test message.

20. A diagnostic procurement system, comprising:
a monitor, for monitoring at least one parameter associated with an entity and communicating data representing said at least one entity parameter, wherein said entity comprises a patient and said at least one monitored entity parameters comprises physiological information about said patient; and
a controller, responsive to said data representing said at least one entity parameter, for determining whether anomalous entity operational parameters are present and, in the case of anomalous entity operational parameters being present, procuring a diagnosis from at least one of a predetermined number of experts,
wherein:
said entity comprises a patient;
said at least one monitored entity parameters comprises physiological information about said patient;
said anomalous entity operational parameters provide information useful in the diagnosis of physiological dysfunction in said patient;
said experts comprise health care professionals;
said controller communicates said data representing said at least one entity parameter to each of a plurality of experts;
said controller receives, from at least one said plurality of experts, a respective opinion suggesting an appropriate remediation of said anomalous entity operational parameter; and
said controller aggregates said at least one received respective opinions to form an aggregate opinion, said aggregate opinion comprising at least an aggregated diagnosis of said anomalous entity operational parameter.

21. The diagnostic procurement system of claim 20, wherein said aggregate opinion comprises an aggregated recommendation of treatment to remediate said anomalous entity operational parameter.

22. A diagnostic procurement system, comprising:
a monitor, for monitoring at least one parameter associated with an entity and communicating data representing said at least one entity parameter, wherein said entity comprises a patient and said at least one monitored entity parameters comprises physiological information about said patient; and
a controller, responsive to said data representing said at least one entity parameter, for determining whether anomalous entity operational parameters are present and, in the case of anomalous entity operational parameters being present, procuring a diagnosis from at least one of a predetermined number of experts,
wherein:
said entity comprises a patient;
said at least one monitored entity parameters comprises physiological information about said patient;
said anomalous entity operational parameters provide information useful in the diagnosis of physiological dysfunction in said patient;
said experts comprise health care professionals; and
said controller comprise health care professionals; and
said controller procures said diagnosis by offering compensation to said at least one said predetermined number of experts in exchange for providing said diagnosis.

23. The diagnostic procurement system of claim 22, wherein the offered compensation comprises a compensation based on one of a fixed compensation amount and a compensation rate.

24. A diagnostic procurement system, comprising:
a monitor, for monitoring at least one parameter associated with an entity and communicating data representing said at least one entity parameter, wherein said entity comprises a patient and said at least one monitored entity parameters comprises physiological information about said patient; and
a controller, responsive to said data representing said at least one entity parameter, for determining whether anomalous entity operational parameters are present and, in the case of anomalous entity operational parameters being present, procuring a diagnosis from at least one of a predetermined number of experts,
wherein:
said controller communicates with said at least one of said predetermined number of experts by causing the transmission of an offer to at least one paging device physically proximate at least one of said predetermined number of experts and receiving, via a return communication, any acceptance of said offer.

25. The diagnostic procurement system of claim 24, wherein:
said controller, after receiving an acceptance from said at least one expert, causes said anomalous entity operational parameters to be available to said at least one expert via a communications medium;
said at least one expert, after communicating said acceptance with said controller, retrieves said anomalous entity operational parameters via said communications medium, renders an expert opinion regarding entity dysfunction, and communicates said expert opinion to said controller via said communications medium.

26. The system of claim 25, wherein said communications are effected via one of the internet, a telecommunications network, a microwave link, a satellite link, a wireless communication medium, and a non-wireless communications medium.

27. A diagnostic procurement system, comprising:
a monitor, for monitoring at least one parameter associated with an entity and communicating data representing said at least one entity parameter, wherein said entity comprises a patient and said at least one monitored entity parameters comprises physiological information about said patient;

a controller, responsive to said data representing said at least one entity parameter, for determining whether anomalous entity operational parameters are present and, in the case of anomalous entity operational parameters being present, procuring a diagnosis from at least one of a predetermined number of experts; and a medical facility, associated with said at least one expert and comprising infrastructure suitable for remediating physiological dysfunction; wherein:

said entity comprises a patient;

said at least one monitored entity parameters comprises physiological information about said patient;

said anomalous entity operational parameters provide information useful in the diagnosis of physiological dysfunction in said patient;

said experts comprise health care professionals; and said controller procures said diagnosis by causing the transmission of an offer to said at least one expert via said medical facility, said medical facility adapting said offer according to a level of facility utilization and a level of physiological dysfunction urgency associated with said offer.

28. The diagnostic procurement system of claim 27, wherein:

said medical facility, in response to said level of utilization being above a threshold level and said level of physiological dysfunction urgency being below a threshold level, causes said offer to be transferred to an alternate medical facility for processing.

29. The diagnostic procurement system of claim 28, wherein said medical facility communicates to said controller the occurrence of a transfer of said offer to said alternate medical facility.

30. The diagnostic procurement system of claim 27, further comprising:

a central server, operably coupled each of a plurality of controllers and a plurality of medical facilities, for facilitating communications between said controllers and said medical facilities; wherein said central server, in response to an offer received from a controller, determines which one of said plurality of medical facilities should receive said offer and communicates said offer to said determined medical facility.

31. The diagnostic procurement system of claim 30, wherein said determination of said central server is made using at least one of the following criteria applied to said medical facilities: proximity to a patient, utilization level, level of expertise in treating an indicated physiological dysfunction, possession of equipment suitable for treating an indicated physiological dysfunction, membership in a predetermined health care provider group, and participation in a predetermined insurance plan.

32. The diagnostic procurement system of claim 24, wherein:

said controller, after receiving an acceptance from said at least one expert, causes said anomalous entity operational parameters to be available to said expert via a communications medium; and said expert, after providing said acceptance to said controller, retrieves said anomalous entity operational parameters via said communications medium, renders an expert opinion regarding entity dysfunction, and communicates said expert opinion to said controller via said communication medium.

33. The diagnostic procurement system of claim 23, wherein:

said monitor utilizes said anomalous entity operational parameters to identify precursor conditions indicative of at least one physiological dysfunction and communicates said identified precursor conditions to said controller.

34. The diagnostic procurement system of claim 24, wherein said monitor utilizes said anomalous entity operational parameters to estimate a time of occurrence of said physiological dysfunction.

35. The diagnostic procurement system of claim 14, further comprising:

a drug dispensing device, for delivering a medicinal compound to said patient in response to a command provided by said controller.

36. The diagnostic procurement system of claim 14, further comprising:

a defibrillator, for delivering to said patient an electrical stimulation in response to a command provided by said controller.

* * * * *